US008698885B2

(12) United States Patent
DiCarlo et al.

(10) Patent No.: US 8,698,885 B2
(45) Date of Patent: Apr. 15, 2014

(54) METHODS AND APPARATUS FOR DEMOSAICING IMAGES WITH HIGHLY CORRELATED COLOR CHANNELS

(75) Inventors: Jeffrey DiCarlo, Menlo Park, CA (US); David D. Scott, Oakland, CA (US); Wenyi Zhao, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 459 days.

(21) Appl. No.: 13/027,071

(22) Filed: Feb. 14, 2011

(65) Prior Publication Data
US 2012/0206582 A1  Aug. 16, 2012

(51) Int. Cl.
*A61B 1/04* (2006.01)
*G06K 9/00* (2006.01)
*G06K 9/32* (2006.01)

(52) U.S. Cl.
USPC .............. 348/71; 382/167; 382/162; 382/300

(58) Field of Classification Search
None
See application file for complete search history.

(56) References Cited

U.S. PATENT DOCUMENTS

| | | | |
|---|---|---|---|
| 3,971,065 A | 7/1976 | Bayer | |
| 5,815,159 A | 9/1998 | Katayama et al. | |
| 6,091,851 A * | 7/2000 | Acharya | 382/167 |
| 7,502,505 B2 * | 3/2009 | Malvar et al. | 382/162 |
| 8,340,407 B2 * | 12/2012 | Kalman | 382/162 |
| 8,441,562 B1 * | 5/2013 | Szedo et al. | 348/280 |
| 2003/0169353 A1 * | 9/2003 | Keshet et al. | 348/272 |
| 2005/0200733 A1 * | 9/2005 | Malvar | 348/272 |
| 2008/0024596 A1 * | 1/2008 | Li et al. | 348/47 |
| 2008/0065105 A1 | 3/2008 | Larkin et al. | |
| 2009/0010539 A1 * | 1/2009 | Guarnera et al. | 382/167 |
| 2009/0088773 A1 * | 4/2009 | Zhao et al. | 606/130 |
| 2009/0252411 A1 * | 10/2009 | Siddiqui et al. | 382/167 |
| 2010/0182415 A1 * | 7/2010 | Elster et al. | 348/77 |

OTHER PUBLICATIONS

Losson, Olivier, Ludovic Macaire, and Yanqin Yang. "Comparison of color demosaicing methods." Advances in Imaging and Electron Physics 162 (2010): 173-265.*
Chang, Lanlan, and Yap-Peng Tan. "Effective use of spatial and spectral correlations for color filter array demosaicking." Consumer Electronics, IEEE Transactions on 50.1 (2004): 355-365.*
Emura, Fabian et al., "Narrow-band imaging optical chromocolonoscopy: Advantages and limitations," World Journal of Gastroenterology, Aug. 21, 2008, vol. 14, No. 31, pp. 4867-4872, The WJG Press.

(Continued)

*Primary Examiner* — Joseph Ustaris
*Assistant Examiner* — Rebecca Volentine

(57) ABSTRACT

In one embodiment of the invention, an apparatus is disclosed including an image sensor, a color filter array, and an image processor. The image sensor has an active area with a matrix of camera pixels. The color filter array is in optical alignment over the matrix of the camera pixels. The color filter array assigns alternating single colors to each camera pixel. The image processor receives the camera pixels and includes a correlation detector to detect spatial correlation of color information between pairs of colors in the pixel data captured by the camera pixels. The correlation detector further controls demosaicing of the camera pixels into full color pixels with improved resolution. The apparatus may further include demosaicing logic to demosaic the camera pixels into the full color pixels with improved resolution in response to the spatial correlation of the color information between pairs of colors.

22 Claims, 16 Drawing Sheets

(56) References Cited

OTHER PUBLICATIONS fileformat.info, "Color," 5 pages, Downloaded Oct. 27, 2010. Internet: http://www.fileformat.info/mirror/egff/ch02_03.htm.
fileformat.info, "Overlays and Transparency," 2 pages, Downloaded Oct. 27, 2010. Internet: http://www.fileformat.info/mirror/egff/ch02_04.htm.
fileformat.info, "Pixel Data and Palettes," 9 pages, Downloaded Oct. 27, 2010. Internet: http://www.fileformat.info/mirror/egff/ch02_02.htm.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

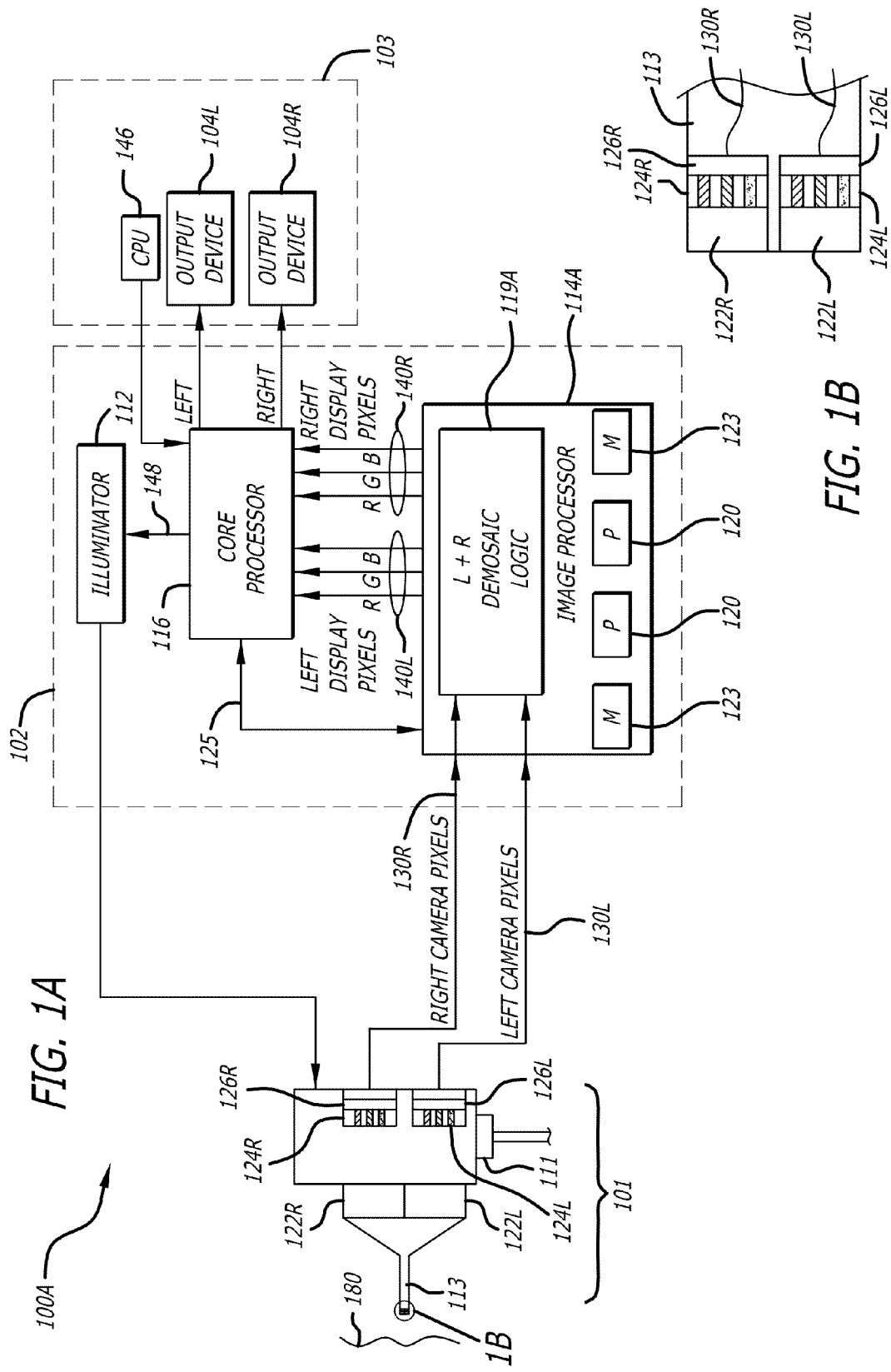

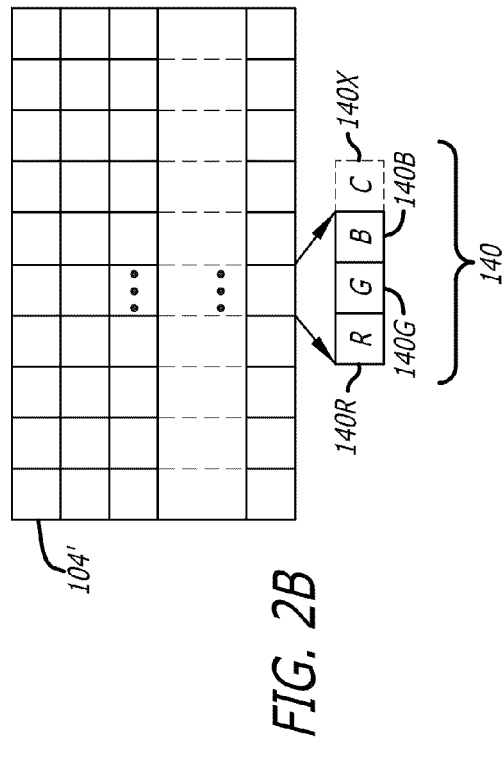
FIG. 2A
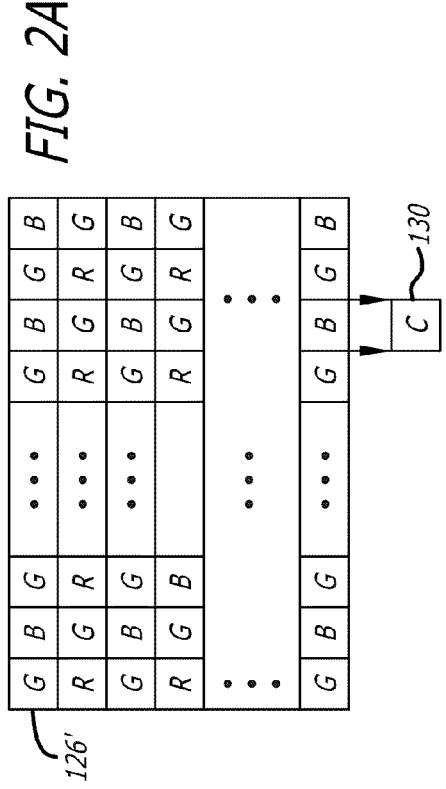
FIG. 2B
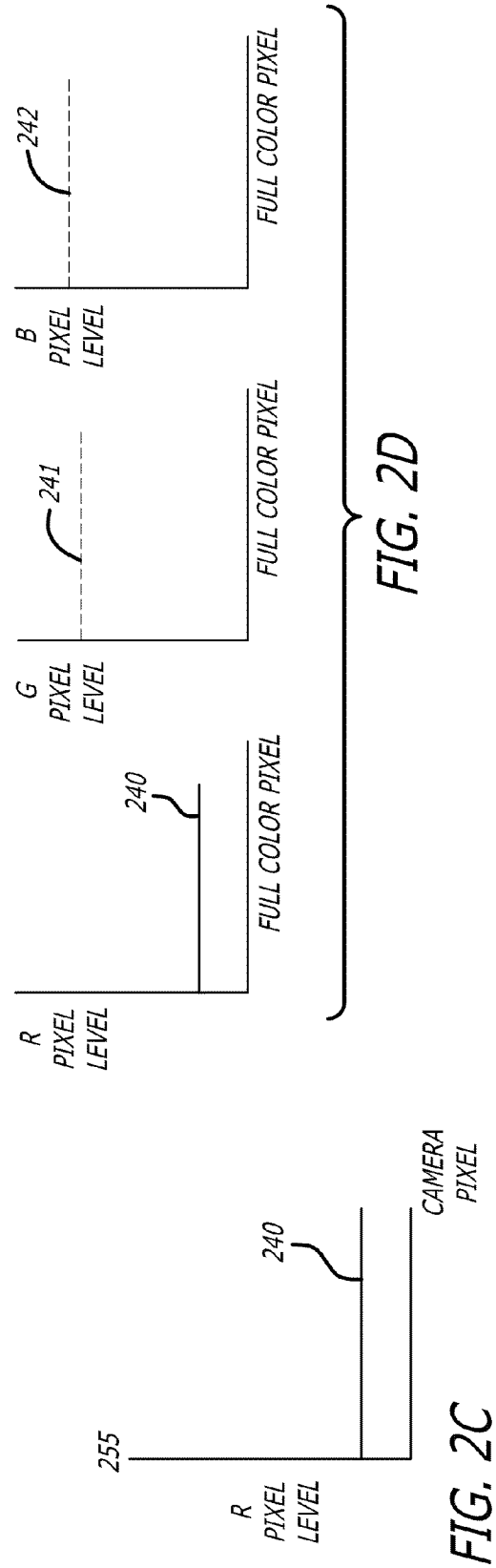
FIG. 2C
FIG. 2D

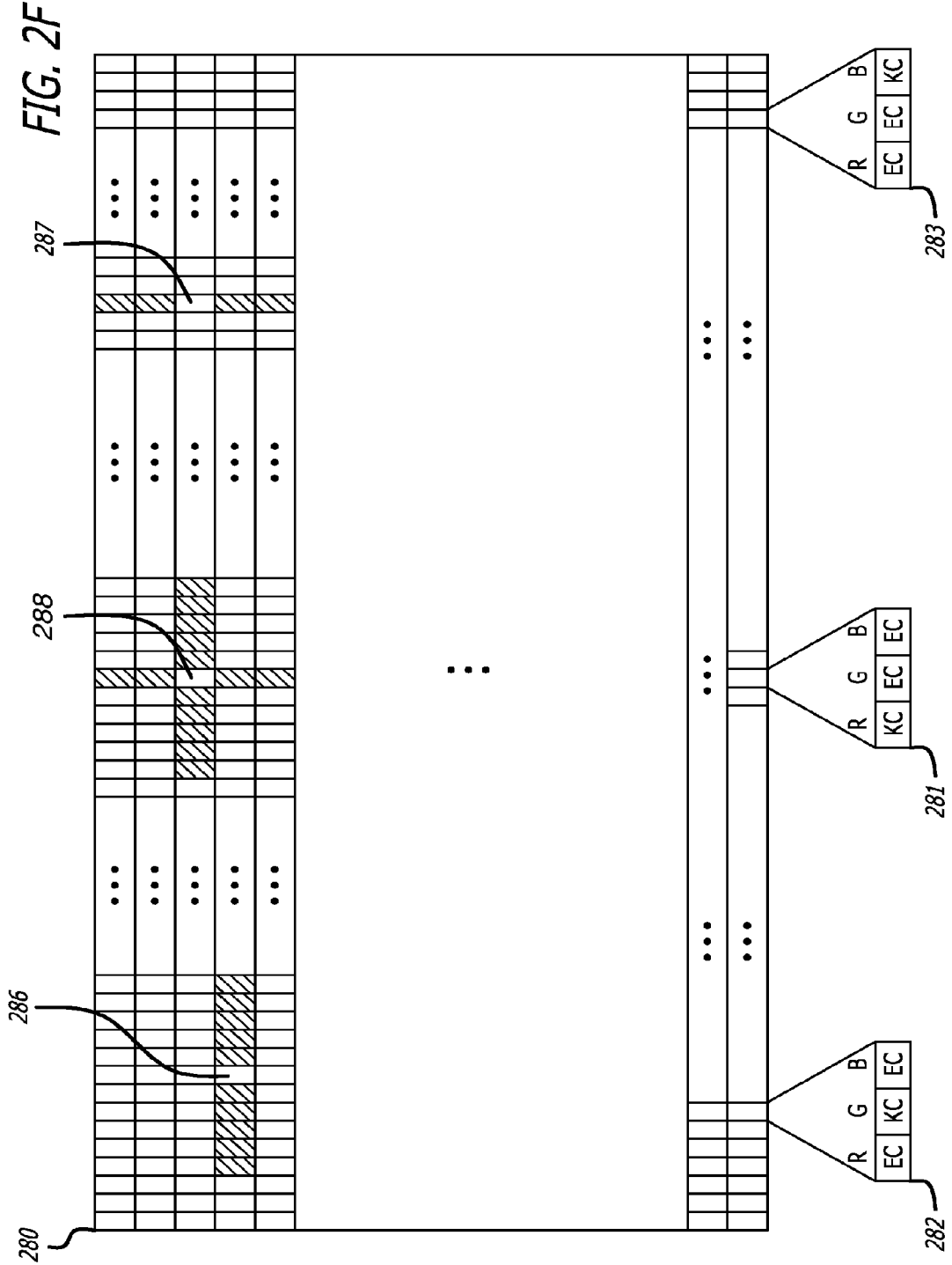

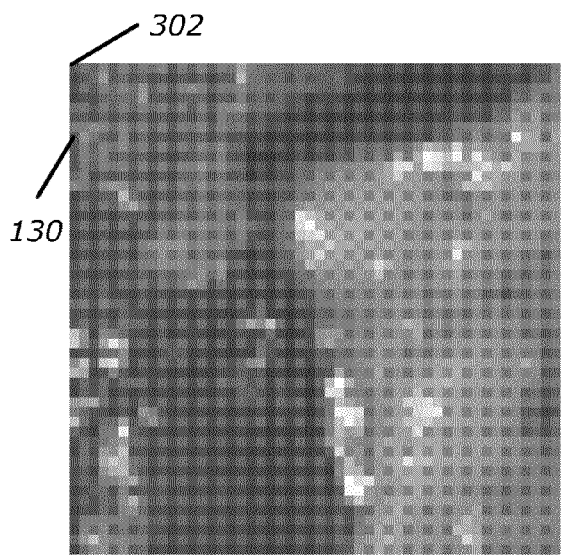
FIG. 3A
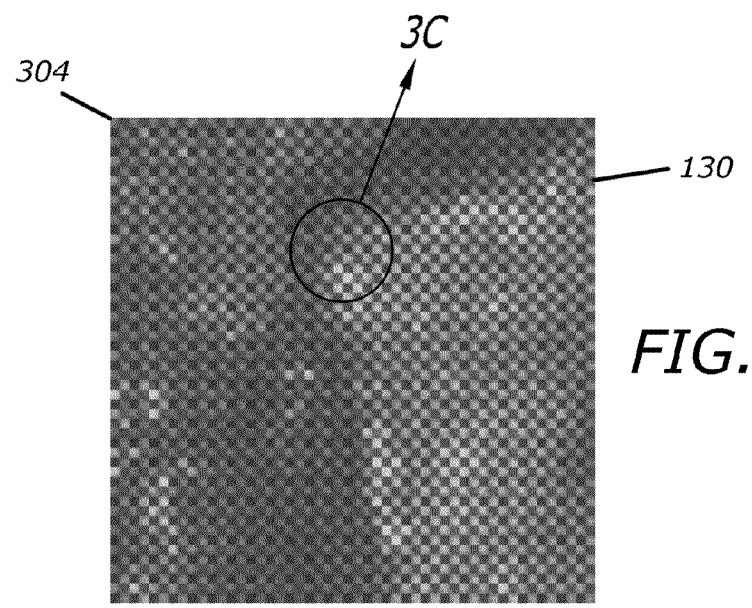
FIG. 3B
FIG. 3C

BEFORE

AFTER

METHODS AND APPARATUS FOR DEMOSAICING IMAGES WITH HIGHLY CORRELATED COLOR CHANNELS

FIELD

The embodiments of the invention generally relate to demosaicing images to generate full color images.

BACKGROUND

Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

To view a surgical site, an endoscopic camera with an illumination means may be inserted into a patient's body. An image sensor in the endoscopic camera captures color images of the surgical site. The small dimensions of the end of the endoscopic camera can limit the size of the image sensor down to a single integrated circuit chip with a limited number of camera pixels. It is difficult to capture high-resolution color images with a single chip with such limited dimensions.

The color images of the surgical site may be shown to a surgeon on a monitor or a display. A surgeon may want to see a magnified region of the color images captured by the image sensor. A digital zoom may be used to magnify the region. While a digital zoom may magnify regions of the images captured by the sensor, a loss of resolution or sharpness in the magnified region can occur.

It is desirable to provide a high-resolution image output to display on a display device from images captured by an image sensor.

BRIEF SUMMARY

The embodiments of the invention are summarized by the claims that follow below.

BRIEF DESCRIPTION OF THE DRAWINGS

FIGS. 1A-1B are block diagrams of stereo imaging systems for minimally invasive surgery employing correlation demosaicing algorithms.

FIG. 2A is a pictorial diagram of an array of camera pixels having a single color per pixel.

FIG. 2B is a pictorial diagram of an array of display pixels having three colors per pixel.

FIGS. 2C and 2D are exemplary charts illustrating pixel data levels for single color camera pixels and full color pixels (tri color pixels).

FIG. 2F illustrates an exemplary correlation map for each camera pixel in a frame.

FIGS. 3A, 3B, and 3C illustrate how a single color is assigned to each camera pixel by a mosaic color filter.

Similar reference numbers in the different drawings are associated with the same or similar elements but may have a different configuration.

DETAILED DESCRIPTION

Figure 1C:
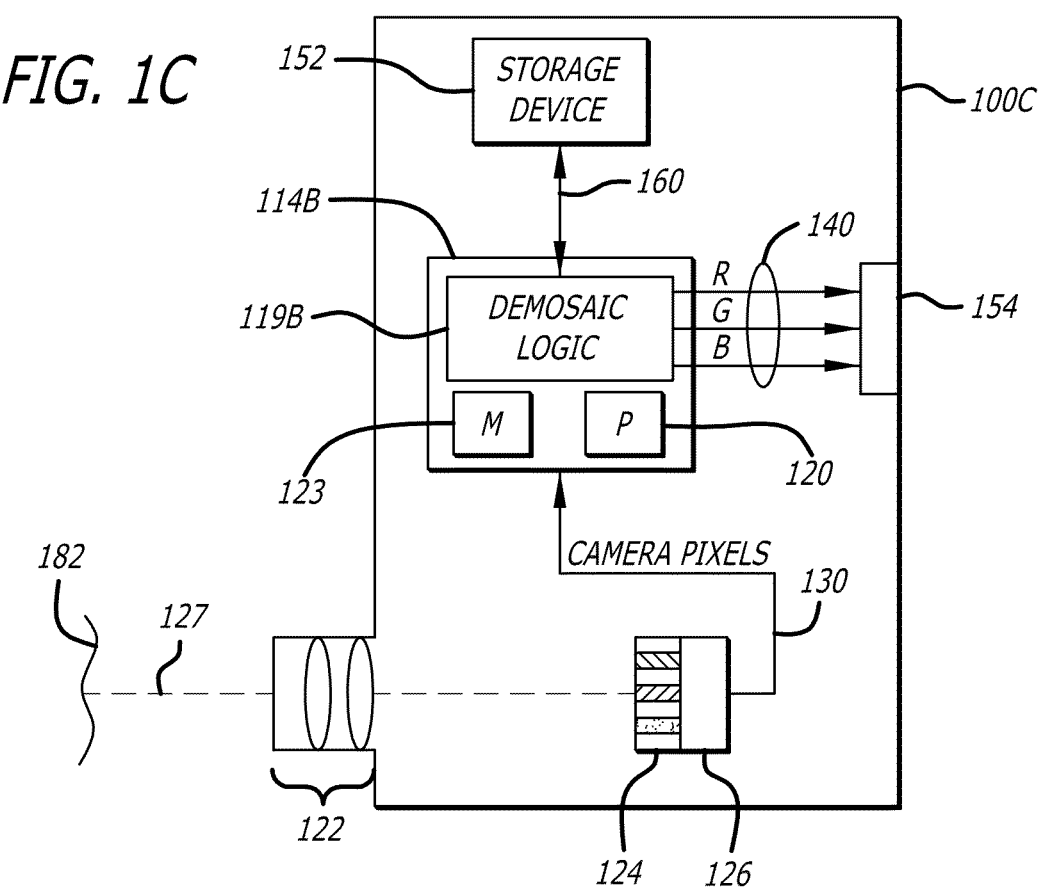
FIG. 1C is a block diagram of a mono imaging system employing correlation demosaicing algorithms.

This detailed description describes exemplary implementations that are illustrative of the invention, and so is explanatory and not limiting. The invention is limited only by patented claims. In the drawings, some elements have been omitted to more clearly show the embodiments of the invention.

Introduction

The embodiments of the invention include a demosaicing algorithm that can produce higher resolution full color images when a pair of color channels is highly correlated in an array of camera pixels. When the pair of color channels is highly correlated, the pair of color channels may be considered effectively equal within a fixed scale factor. For example, statistics of medical scenes (e.g., images of surgical sites inside the body) may have a high degree of spatial correlation between color channels of pixel data (e.g., green and blue color channels in an RGB color system; other color systems may be used). Thus with medical images, these color channels may be considered to change equally from pixel location to pixel location.

In accordance with an aspect of the invention, if a high correlation between first color channel information and second color channel information likely exists for a pixel of interest, and if the first color channel information is known and the second color channel information is missing (e.g., because only the first color channel information is captured at the pixel of interest's location), then a demosaicing process uses the known first color channel information to estimate missing second color channel information for the pixel of interest. Since the estimated second color channel information is based on known information at the pixel of interest's location, rather than on known information from pixel locations surrounding the pixel of interest, the estimate is more accurate than prior art processes. If a high correlation between the first color channel information and the second color channel information does not exist for a pixel of interest, then known methods are used to estimate the missing second color channel information from second color channel information in pixels surrounding the pixel of interest. A similar process may be used for instances when first and third (and fourth, etc.) color channel information is also highly correlated at the pixel of interest, or for a second highly correlated color channel pair (e.g., third and fourth) at the pixel of interest. Thus, full color channel information for each pixel of interest in an input image is produced, and when color channel information is highly correlated in many input image pixels, this process produces an output image with higher spatial resolution than output images produced only by estimating missing color information from surrounding pixels.

In accordance with an optional aspect of the invention, a color channel correlation map is created for pixel locations within an image. This map is used during the demosaicing processes described herein.

In accordance with a further aspect of the invention, once the missing second color channel information is estimated from the known first color channel information at a pixel of interest, the estimated second color channel information is further refined by using known second color channel information from pixel locations surrounding the pixel of interest. Likewise for third, etc. color channels for the pixel of interest as applicable. Thus, even higher spatial resolution output images can be generated than when only the known color channel information at the pixel of interest is used.

Generally in one embodiment of the invention, a method of demosaicing camera pixels in an array of camera pixels in response to spatial correlation is disclosed. The method may be used for improving the spatial resolution of medical images. One method includes capturing an image from a surgical site within a patient, the captured image including initial pixel data of a plurality of camera pixels; assigning single color information to the initial pixel data of each of the plurality of camera pixels to form mono-color pixel data; in an array of a plurality of arrays of camera pixels, determining if a pair of color channels are substantially correlated, and if the pair of color channels are substantially correlated then demosaicing each camera pixel in the array with its mono-color pixel data to generate full color pixel data for each camera pixel of the plurality to form a full color image with improved resolution; and outputting the full color image with the improved resolution.

Imaging Systems with Demosaic Logic and Algorithms

Referring now to FIG. 1A, a block diagram of an imaging system 100A for minimally invasive surgery is illustrated. The imaging system 100A includes an endoscopic camera 101, a vision control cart 102, and a surgeon console 103 coupled together as shown.

The endoscopic camera 101 includes a mechanical interface to detachably couple to a robotic arm 111 of a patient side manipulator so that it may be moved around within a surgical site of a patient. See for example, U.S. Pat. No. 6,451,027 by Cooper et al.; U.S. Pat. No. 6,779,065 by Niemeyer; U.S. Pat. No. 6,873,883 by Moll et al.; and U.S. Pat. No. 6,331,181 by Tierney et al., all of which are incorporated herein by reference. The robotic arm 111 supports the endoscopic camera 101 within the body cavity of a patient over a surgical site 180. The endoscopic camera 101 is used to capture digital images within the body cavity of the patient. The surgical site 180 includes tissue that can reflect white light to form a typical color medical image when illuminated by visible light. The endoscopic camera captures the image in the form of alternating color pixel data values, also referred to as camera pixels, that can be described as being in different color channels respectively. For example, the series of red camera pixels in different pixel locations within a frame of an image may be described as being the red color channel. An image of tissue is a typical medical image that may have a pair of color channels (e.g., green and blue color channels formed of their respective color camera pixels) with substantial spatial correlation between pixel data values at a number of different pixel locations.

The vision control cart 102 includes an illuminator 112, an image processor 114A, and a core processor 116. The vision control cart 102 may optionally include a display monitor (not shown). The endoscopic camera 101 may be coupled to the illuminator 112 to receive visible light (VL) and direct it out of its tip into the surgical site 180 to visibly illuminate tissue for capture with one or more images sensors 126L-126R. The endoscopic camera 101 captures one or more frames of medical images within the surgical site in response to the visible light (VL) and couples them into the image processor 114A. For stereo imaging, the endoscopic camera 101 is a stereo camera for concurrently capturing left and right images of the surgical site with left and right image sensors 126L-126R.

The illuminator 112 may generate the visible light (VL), a light generated in the visible electromagnetic radiation spectrum, in response to control signals 148 received from the core processor 116. The illuminator 112 may generate the visible light (VL) to capture frames of the visible images (VI) in response to the control signals.

The visible light (VL) may be coupled into the endoscopic camera 101 by one or more optical fibers or bundles of optical fibers. Similarly, the visible images (VI) of visible tissue captured by a sensor within the surgical site may coupled into the image processor 114A via an optical fiber cable or by a wire cable.

The camera pixel data, representing images of tissue within the surgical site 180, is captured by one or more image sensors 126L,126R and coupled into the image processor 114A by one or more cables 130L,130R. The camera pixel data may be alternatively assigned a visible color such as red, green, blue and/or other colors in the electro-magnetic (EM) spectrum or a wavelength in the non-visible EM spectrum (e.g., near-infra-red). This color assignment is responsive to a color mosaic filter aligned over the image sensor.

A left color mosaic filter 124L is mounted over and in optical alignment with the camera pixels in the left image sensor 126L. Left optics 122L (one or more lenses) are mounted over and in optical alignment with the left color mosaic filter 124L and the left image sensor 126L. The right color mosaic filter 124R and right optics 122R (one or more lenses) are mounted over and in optical alignment with the camera pixels in the right image sensor 126R.

The image processor 114A includes one or more processors P 120 to process the captured images and one or more storage devices (e.g., memory) M 123 to store one or more frames of image data. For stereo imaging, the image processor 114A may include a pair of processors P 120 to process left and right captured images and a pair of storage devices (e.g., memory) M 123 to store left and right image frames.

The one or more processors P 120 of the image processor 114A may execute software instructions to perform operations on the pixel data of each frame of digital image data in order to perform the image processing and display methods disclosed herein. The image processor 114A receives commands 125 from the core processor 116 and couples the images to the core processor 116 for display on a left display output device 140L and/or a right display output device 140R of the surgeon console 103 and/or a monitor (not shown) of the vision control cart 102. Alternatively or conjunctively, the core processor 116 may receive digital images and execute software instructions to perform operations on the pixel data of each frame of digital image data in order to perform the image processing and display methods disclosed herein.

The surgeon console 103 may be coupled to the core processor 116 by a fiber optic cable for high-speed communication of digital control and image information. The surgeon console 103 may include a stereo display device formed by the left display output device 140L and the right display output device 140R to display left and right stereo images to the surgeon. Alternatively, the left display output device 140L and the right display output device 140R may provide some other type of user readable output, such as a hard copy print out of photographic images.

Further information regarding minimally invasive surgical systems may be found for example in U.S. patent application Ser. No. 11/762,165, entitled MINIMALLY INVASIVE SURGICAL SYSTEM, filed by David Q. Larkin et al. on Jun. 13, 2007, published as US Patent App. Publication 2008/0065105; and U.S. Pat. No. 6,331,181, entitled SURGICAL ROBOTIC TOOLS, DATA ARCHITECTURE, AND USE, issued to Tierney et al. on Dec. 18, 2001, both of which are incorporated herein by reference.

In FIG. 1A, the left and right image sensors 126L-126R are located in the camera housing near a proximal end of the endoscope 101 that mounts to the robotic arm 111. Alternatively, the image sensors may be mounted within the shaft 113 of the endoscope 101 that is inserted within a patient. Camera pixel data from the camera pixels of the image sensors may be transmitted over cables within the shaft out of the patient's body.

Referring now to FIG. 1B, a left image sensor 126L and a right image sensor 126R are illustrated as being mounted within the shaft 113 near the distal end of endoscope 101. A left color mosaic filter 124L is mounted over the camera pixels in the left image sensor 126L. Left optics 122L (one or more lenses) are mounted over the left color mosaic filter 124L. The right image sensor 126R is similarly mounted within the shaft 113 next to the left image sensor 126L near the distal end of the endoscope. A right color mosaic filter 124R and right optics 122R (one or more lenses) are mounted over the camera pixels in the right image sensor 126R respectively next to the left color mosaic filter 124L and the left optics 122L.

Cables 130L,130R are coupled to the image sensors 126L, 126R to respectively send the left camera pixel data and the right camera pixel data through the shaft 113 of the endoscope out to the image processor 114A.

In FIG. 1A, the image processor 114A receives left camera pixels and right camera pixels from the left and right image sensors 126L-126R respectively. The image processor 114A includes left and right demosaic logic 119A to execute left and right demosaicing algorithms to independently process left camera pixels and right camera pixels for left and right images of a stereo image. The image processor 114A is coupled to the core processor 116.

The demosaic logic 119A receives the left camera pixels over the cable 130L and generates left full color pixels 140L. The demosaic logic 119A receives the right camera pixels over the cable 130R and generates right full color pixels 140R. The core processor 116 receives the left full color pixels 140L and may assemble a plurality of them together into a frame of left full color pixels 140L to form a left image frame for display. Similarly, the core processor 116 receives the right full color pixels 140R and may assemble a plurality of them together into a frame of right full color pixels 140R to form a right image frame for display. A plurality of left and right image frames may be assembled together over time to display stereo video images.

The core processor 116 may couple to a left output device 104L and a right output device 104R of a stereo display device in the surgeon console 103. The left display pixels 140L are coupled into the left output device 104L. The right display pixels 140R are coupled to the right output device 104R. In this manner frames of images may be displayed in time on the output devices 140L,140R.

The core processor 116 may further couple to a control processor 146 of the surgeon console 103 to receive control signals to control the imaging system 100A.

Referring now to FIG. 1C, an alternate imaging system 100C is illustrated. The imaging system 100C has a single image sensor 126 to form a mono-image and may be a digital camera for example. The imaging system 100C further includes a color filter array 124 (also referred to as a color mosaic filter) mounted over the image sensor 126 in alignment along an optical axis 127. Optics 122 (one or more lenses) are mounted over the color filter array 124 and the image sensor 126 in alignment along the optical axis 127 as well. The optics may provide variable focus and/or an optical zoom capability.

The imaging system 100C further includes an image processor 114B. The image sensor 126 is coupled to the image processor 114B by a cable so that pixel data of the camera pixels 130 can be communicated from the image sensor 126 to the image processor 114B. The image processor 114B includes a processor P 120 to process the captured images and a storage device (e.g., memory) M 123 to store image frames for further processing.

The system 100C further includes a liquid crystal display (LCD) 154 coupled to the image processor 114B. The system 100C may optionally include a storage device 152 coupled to the image processor 114B. The storage device may store raw camera pixel data 130 and/or display pixel data 160. The image processor 114B includes demosaic logic 119B that receives the camera pixel data 130 and executes demosaicing algorithms to generate the full color pixels 140 for display on the liquid crystal display 154 or full color pixels 160 for storage into the storage device 152. Aspects of the demosaicing algorithms performed by the demosaic logic 119B are further described herein.

Medical Scenes

Figure 1D:
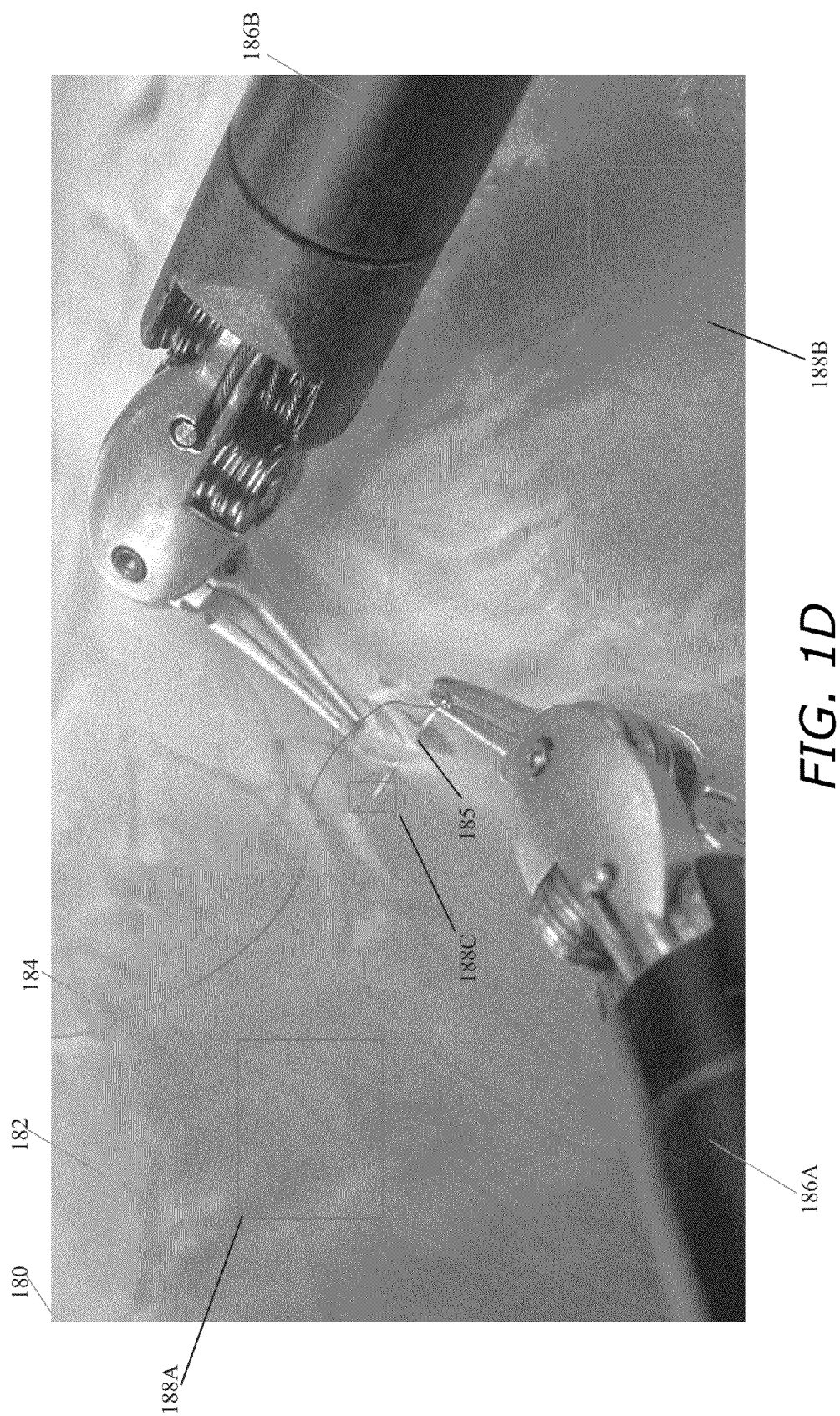
FIG. 1D is a frame of a medical scene of a surgical site illustrating differing array sizes and differing objects found within a surgical site.

Referring now to FIG. 1D, an image or frame 180 of an exemplary medical scene of a surgical site is illustrated. The medical scene includes differing objects found within a surgical site. For example, a typical medical scene may include tissue 182, suture 184, needle 185, and one or more surgical tools 186A-186B. In analyzing captured data representing a medical image within a frame, differing array sizes may be used depending upon the homogeneous nature of the objects within the medical scene. For example, if tissue color and texture are regular, a larger array 188A of pixels may be used to analyze color information to provide improved resolution in a full color image. If tissue color and texture are less regular or less homogeneous, a smaller array 188B of pixels may be used to analyze color information to provide improved resolution in a full color image, for example. If there is significant change in features, such as where a needle is inserted through tissue, an even smaller array 188C of pixels may be used to analyze color information to provide improved resolution in a full color image, for example.

Demosaicing

Referring now to FIG. 2A, a frame 126' of M by N single color camera pixels 130 is illustrated. As its name implies, a single color camera pixel 130 has only one color associated with it. Each respective single color for each camera pixel 130 is assigned by the overlying color of the mosaic filter 124, 124L,124R that is over them. The single color may be red, green, or blue for example. Other colors may also be utilized, such as yellow, for higher definition. However, primary colors of red, green, or blue have been the traditional single colors alternatively assigned to a camera pixel with all three being assigned to a full color pixel. Note that some aspects of the invention are explained herein using the traditional three primary colors of red, green, and blue, such as shown by the frame 126' of M by N single color camera pixels 130. However, aspects of the invention are not restricted to the use of three colors, but may be adapted to using two, three, four or more different colors to assign alternating single colors to the camera pixels.

Referring now to FIG. 2B, a frame 104' of full color pixels 140 is illustrated. A full color pixel 140 may include a red sub-pixel 140R, a green sub-pixel 140G, and a blue sub-pixel 140B. Alternatively, a full color pixel 140 may further include additional color sub-pixels, such as sub-pixel C 140X for example.

The full color pixel 140 is generated from the single color camera pixel 130. In one or more embodiments of the invention, the full color pixel 140 is generated by demosaicing logic with demosaicing algorithms in response to a substantial correlation in a pair of color channels within an array of X by Y single color camera pixels. The array of camera pixels are found within the frame 126' of camera pixels 130. Depending upon the image sensors being used, the frame of camera pixels 126' and the frame of full color pixels 140' may be M pixels by N pixels (M and N being variable depending upon the image sensor) to provide a high definition format.

Referring now to FIG. 2C, a graph of a single color level 240 (e.g., red, green, or blue) for the known color (KC) of a given single color camera pixel 130 is shown. There is no level of color for the missing colors (MC) because this is the missing information in the camera pixel that is to be interpolated. Assuming the color level 240 is representative of a red camera pixel 130 in the one frame 126', the color levels for blue and green are at least missing. The level and pixel data representing the known color are used during interpolation to determine the two missing color levels and pixel data representative of the missing color from the camera pixel.

Referring now to FIG. 2D, exemplary graphs 240,241,242 for a given full color pixel 140 are illustrated. Each graph indicates levels of red, green, and blue colors greater than a level of zero for the full color pixel 140. While a color level may be zero, there is no missing color level or pixel data in the full color pixel 140. The levels of at least two of the colors in the full color pixel 140 are interpolated from the single color of the camera pixel 130. For example, if the red color was the known color (KC) represented by graph 240, the missing colors (MC) of blue and green are interpolated from the red color and its level to generate the levels 241 and 242 to complete the full color pixel. The plots 240,241,242 have color levels associated with each respective color sub-pixel in the full color pixel.

Figure 2E:
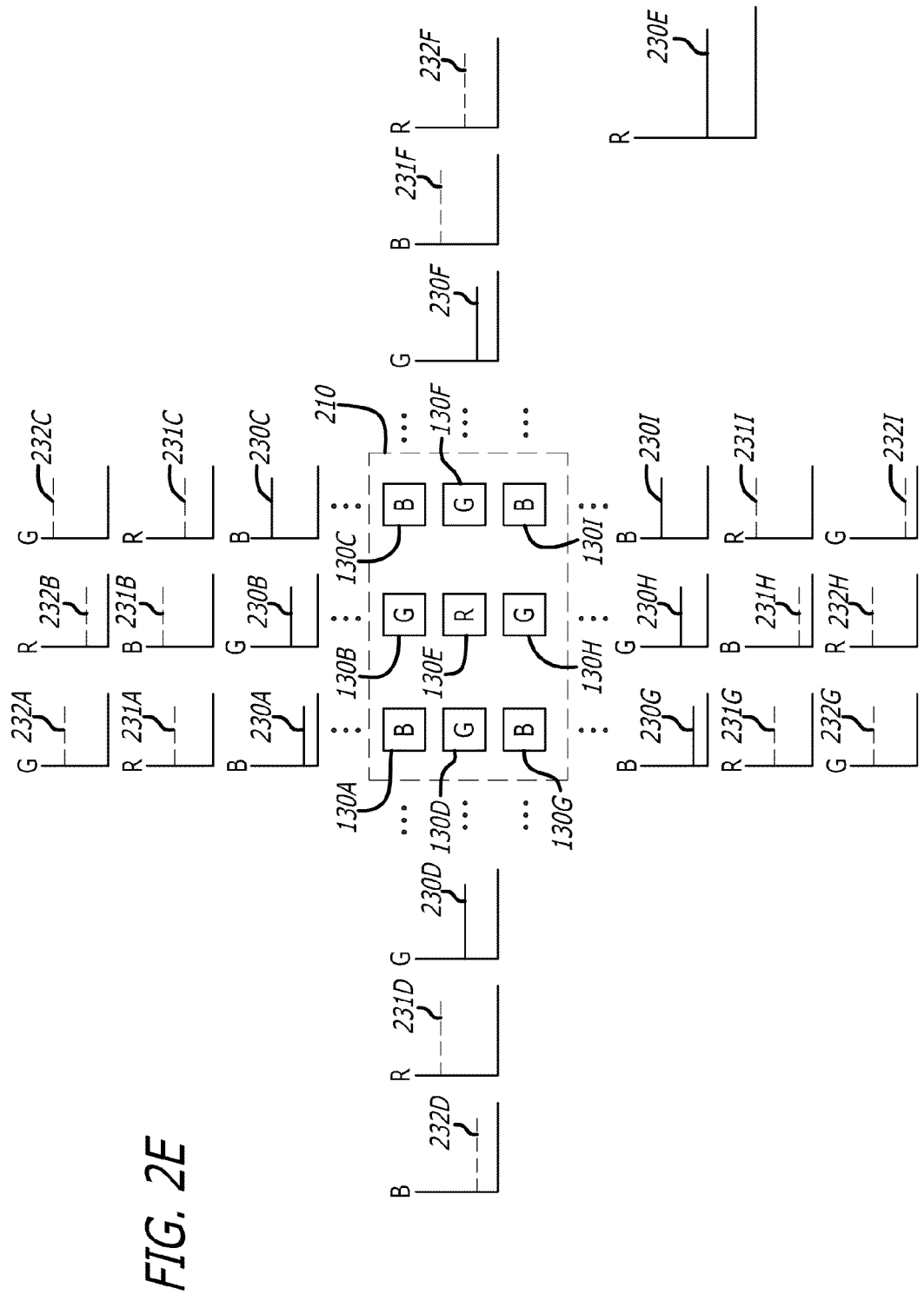
FIG. 2E is a pictorial diagram to illustrate how pixel data levels for the camera pixels may vary from pixel location to pixel location and be spatially correlated or not.

Referring now to FIG. 2E, an exemplary three by three array 210 of camera pixels 130 is illustrated. The array 210 includes camera pixels 130A-130I. Also shown in FIG. 2E are charts of the known single color levels 230A-230I for each respective camera pixel 130A-130I. The exemplary array of camera pixels and associated charts of color levels for each is shown to illustrate spatial correlation between camera pixels and color channels.

The camera pixels 130A and 130B, for example, have known color levels 230A and 230B respectively. The camera pixel 130C has a color level 230C, for example. In comparison with the color level 230C of the camera pixel 130C, the camera pixels 130A and 130B may have substantially correlated color levels 230A, 230B because they change similarly in a spatial manner from camera pixel location to camera pixel location. Similarly the color levels 230H, 230I associated with the green (G) camera pixel 130H and the blue (B) camera pixel 130I may be substantially correlated because their levels change nearly the same from pixel location to pixel location.

Referring now to FIG. 2F, an exemplary correlation map for a frame 280 of camera pixels is illustrated. The missing color information in each camera pixel is estimated and stored with the known color information. For a camera pixel 281, for example, the correlation map stores known color information (KC) for red, estimated color information (EC) for green, and estimated color information (EC) for blue. For a camera pixel 282, for example, the correlation map stores known color information (KC) for green, estimated color information (EC) for blue, and estimated color information (EC) for red. For a camera pixel 283, for example, the correlation map stores known color information (KC) for blue, estimated color information (EC) for red, and estimated color information (EC) for green. The missing color information for each camera pixel may be estimated in a number of different ways.

As the correlation map is to be used to determine spatial correlation between a pair of color channels (e.g., red/blue, red/green, blue/green color channels), a low-resolution estimation may be used such as an interpolation algorithm or a blurring filter to estimate the missing color information for each camera pixel in the frame to complete the correlation map. An interpolation or averaging technique over neighboring camera pixels may be used to determine the missing color information for a current camera pixel. Neighboring pixels refers to any pixels that are in the local area of the pixel of interest, including a pixel that may be multiple pixels away from the given pixel of interest. Bordering pixels refers to those pixels that are immediately adjacent or touching the give pixel of interest.

Consider camera pixel 286 for example, assuming the known color information to be red. Green color information can be estimated using the green color information from the neighboring horizontal camera pixels for example. Xl neighboring camera pixels to the left and Xr neighboring camera pixels to the right may be used to interpolate or average the green color information for the current camera pixel 286. Blue color information may be estimated for the current camera pixel 286 using the blue color information from the neighboring horizontal camera pixels, for example. As alternating camera pixels have known color information for a given color, the total of neighboring camera pixels Xl and Xr should be sufficiently large to average by dividing by at least by 2. For example, five neighboring horizontal camera pixels may be chosen on the left and right to average and determine the missing color information by dividing by at least two. Typically the same color of camera pixels are used to average and determine the missing color information given the alternating nature of the color information in the camera pixels, such as shown in FIG. 2A. However, known color information from differing colors of camera pixels may also be used to average and determine the missing color information for a given camera pixel. Assume that the color information ranges in values from 0 to 255 and six known color values of neighboring camera pixels of the same color are 5, 10, 15, 35, 45, and 100. To compute an average, the known color values of neighboring camera pixels are summed together and divided by the number of neighboring camera pixels used to generate the sum. In this example of six camera pixels, the average may be computed from 210 divided by 6 equaling 35. Computing averages such as this results in known red color information (KC), estimated blue color information (EC), and estimated green color information (EC), such as shown by the full color pixel 281 in FIG. 2F.

Consider camera pixel 287 for example, assuming the known color information (KC) to be green. Red color information can be estimated (EC) using the known red color information from the neighboring vertical camera pixels for example. Yu neighboring camera pixels above and Yb neighboring camera pixels below may be used to interpolate or average the red color information for the current camera pixel 287. Blue color information may be estimated (EC) for the current camera pixel 287 using the blue color information from the neighboring vertical camera pixels, for example. As alternating camera pixels have known color information for a given color, the total of neighboring camera pixels Yu and Yb should be sufficiently large to average by dividing by at least by 2. This results in estimated red color information (EC), known green color information (KC), and estimated blue color information (EC), such as shown by the full color pixel 282 in FIG. 2F.

Consider camera pixel 288 for example assuming the known color (KC) information to be blue. Red color information can be estimated (EC) using the known red color information from the neighboring vertical camera pixels and neighboring horizontal camera pixels for example. Yu neighboring camera pixels above, Yb neighboring camera pixels below, Xl neighboring camera pixels to the left, and Xr neighboring camera pixels to the right may be used to interpolate or average the red color information for the current camera pixel 288. Blue color information may be estimated (EC) for the current camera pixel 288 using the blue color information from the neighboring vertical camera pixels and neighboring horizontal camera pixels, for example. As alternating camera pixels have known color information for a given color, the total number of neighboring camera pixels Yu, Yb, Xl, and Xr should be sufficiently large to average by dividing by at least by 2. This results in estimated red color information (EC), estimated green color information (EC), and known blue color information (KC), such as shown by the full color pixel 283 in FIG. 2F.

Although not shown in FIG. 2F, neighboring camera pixels on the diagonals may also be used to determine estimated values for color values missing from the neighboring camera pixels to provide a more accurate correlation map. The respective known color values are added together and may be averaged similarly. In another embodiment of the invention, digital filtering may be used on the neighboring camera pixels to determine estimated values for missing color values in the neighboring camera pixels to provide a more accurate correlation map.

Figure 2G:
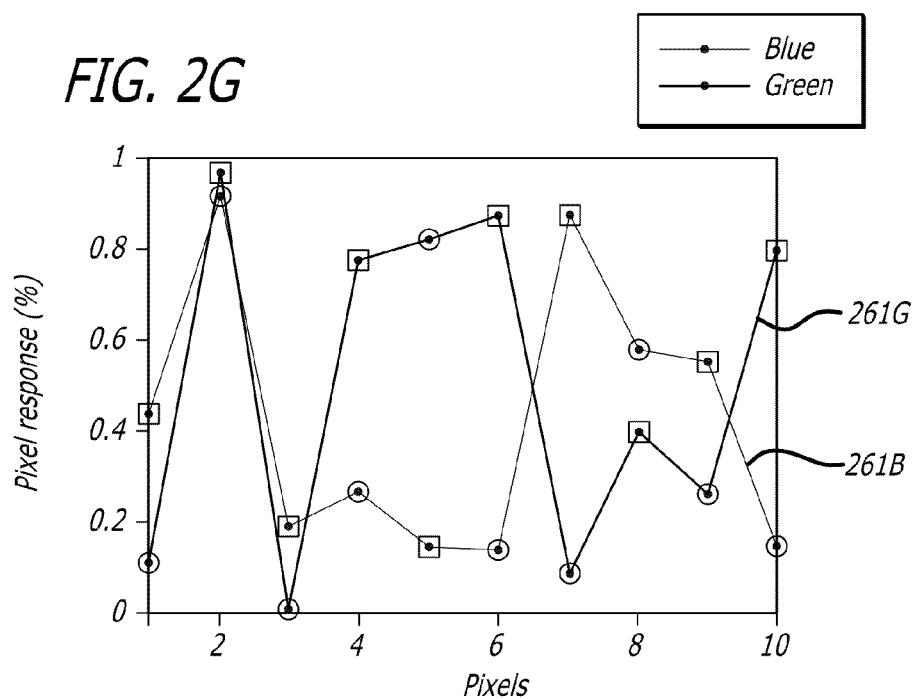
FIG. 2G illustrates a chart of a blue color channel plot, a red color channel plot, and a green color channel plot where the color channels are spatially uncorrelated from pixel location to pixel location in the array.
Figure 2H:
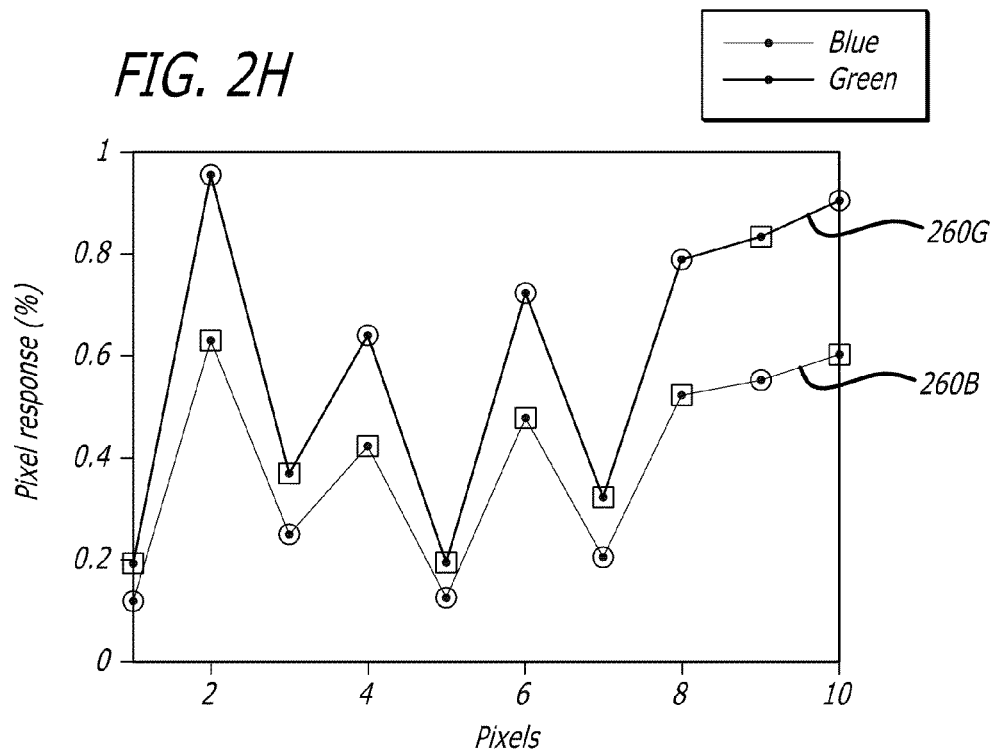
FIG. 2H illustrates a chart of a blue color channel plot, a red color channel plot, and a green color channel plot where the color channels are spatially correlated from pixel location to pixel location in the array.

Referring now to FIGS. 2G and 2H, charts are illustrated of color level percentages versus pixel number location for a 1 by 10 array of pixel locations to better illustrate how a pair of color channels may be substantially correlated over an image captured from a scene. Missing color information in each of the cameral pixels has been estimated as described previously with the points circled on the plot being measured points and the points squared on the plot being estimated points.

FIG. 2G illustrates a blue color channel plot 261B and a green channel plot 261G where the color channels are spatially uncorrelated from pixel location to pixel location in the array. The respective pixel values plotted on the color channel plots 261B and 261G change from pixel location to pixel location in the array without any underlying relatedness or correlation.

In contrast, FIG. 2H illustrates a blue color channel plot 260B and a green channel plot 260G where the pair of color channels are spatially correlated from pixel location to pixel location in the array. The respective pixel values plotted on the color channel plots 260B and 260G similarly change from pixel location to pixel location in the array such that there is substantial correlation between the pair of color channels. In this case, the known color information of one channel may be scaled to obtain a value for the color information of the other channel for the given camera pixel location.

For a given array of camera pixels, levels of correlation between the color channels may be determined from the correlation map. The levels of correlation may be represented as correlation coefficients or weights that are multiplied together with the known color information to determine levels of missing color information for a current camera pixel in the array.

With the color levels of at least a pair of color channels being substantially correlated, interpolation of missing colors in the camera pixel can be made from the known color information for each given camera pixel. For example, assume the red color level 240 in FIG. 2D is the known color information. In which case, the green color level 241 and the blue color level 242 may be interpolated from the known red color level 240 for the given red camera pixel 130E and the correlation coefficients for the missing colors within the selected array.

Consider pixel 130E in FIG. 2E once again with the correlation map being completed. Plots 230A-230D, 230E-230I represent the known color information for neighboring pixels. Plots 231A-231D, 231F-231I represent a first estimated color information for neighboring pixels. Plots 232A-232D, 232F-232I represent second estimated color information for neighboring pixels. The missing color information for the current camera pixel 130E may be interpolated from correlation coefficients between the color channels determined for the camera pixels within the array 210. For example, if plot 240 in FIG. 2D illustrates the known sub-pixel data level of color information, then the interpolated color information that is responsive to the color correlation (e.g., correlation coefficients or weights) may by represented by the sub-pixel data levels illustrated by plots 241 and 242 to form a full color pixel.

A demosaicing process generally takes the known color information for the camera pixel and interpolates the missing color information to form a full color pixel. Initially, pixel data for each of the camera pixels in the frame is captured and assigned single color information in response to a color mosaic filter.

Referring now to FIG. 3A, a frame 302 of M by N gray scale camera pixels 130 is illustrated after being captured by an image sensor. A color mosaic filter (also referred to as a color filter array) initially filters light before the image sensor captures it. The color mosaic filter may have an alternating pattern of primary colors red, green, and blue, for example. The grey scale camera pixels 130 are then assigned the respective color of the color mosaic filter over each. For example, a camera pixel with a red rectangular color filter aligned over it to filter out colors other than red, is assigned to be a red camera pixel.

FIG. 3B illustrates a color mosaic frame 304 of mono or single color camera pixels 130 with a different color spatially from pixel position to pixel position. FIG. 3C illustrates a magnified portion of the frame 304. The magnified portion of the frame illustrates green camera pixels G 130G, red camera pixels R 130R, and blue camera pixels B 130B in differing pixel positions. However, aspects of the invention are not restricted to use of three colors, but may be adapted to using two, three, four or more different colors as the color mosaic filter to assign alternating colors to the single camera pixels.

With single color information assigned to each camera pixel, the homogeneity of the underlying image may be estimated. The homogeneity of the underlying image is useful to determine which direction (horizontal or vertical) does the neighboring pixel from a given pixel change the least. The direction with the least change may be used to select the neighbors from which to interpolate for the missing color information.

Figure 4A:
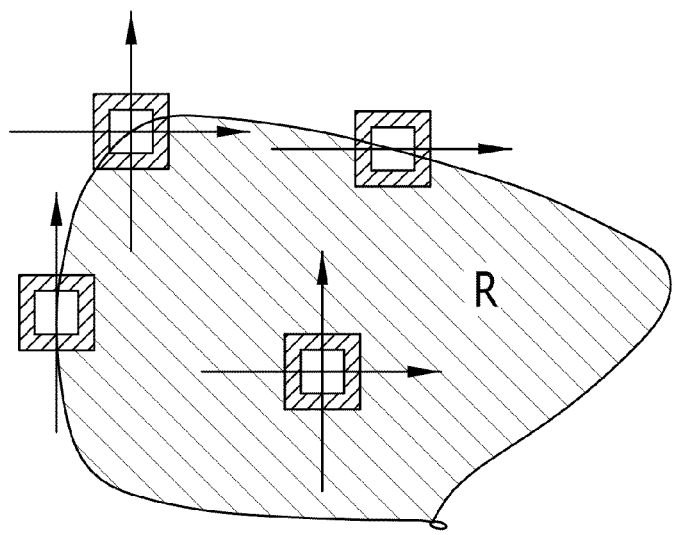
FIGS. 4A-4C illustrates how homogeneity of an underlying image may be estimated within an array of single color camera pixels.

Referring now to FIG. 4A, an image is shown to illustrate how homogeneity can vary. An analysis of the image at differing camera pixel locations is used to determine the homogeneity of the underlying image. Recall that the underlying image is a color mosaic of camera pixels 130. However, the pixel data level over the neighboring camera pixels is used regardless of color to determine if there is little change or significant change in levels in the vertical, horizontal, or both vertical and horizontal directions.

Figure 4B:
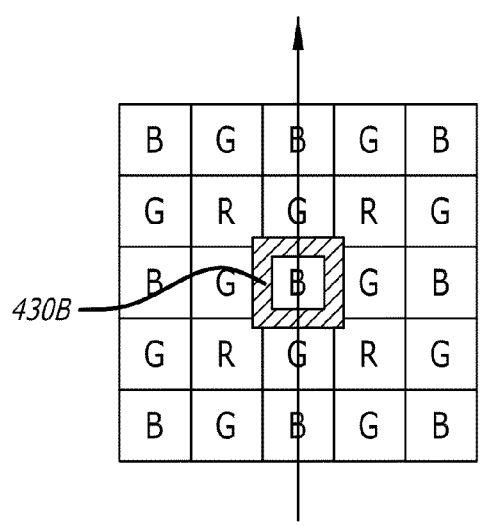
Figure 4C:
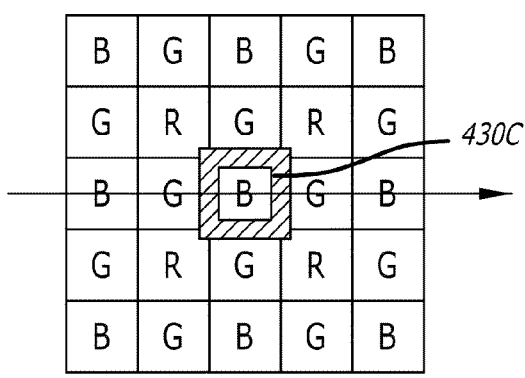

In FIG. 4B for example, the homogeneity at camera pixel 430B may be estimated by comparing pixel data along a vertical line through the camera pixels above and below the camera pixel 430B. In FIG. 4C for example, the homogeneity at camera pixel 430C may be measured by comparing pixel data along a horizontal line of camera pixels to the left and the right of the given camera pixel 430C.

Estimating the homogeneity of an image differs from determining correlation of a pair of color channels in an array of pixels. Homogeneity is measured along a column and/or a row of camera pixels through a given camera pixel. The color of the single camera pixel is irrelevant. In contrast, correlation is measured over an M by N array of camera pixels. Moreover, the correlation is measured between color channels such that the color of the camera pixel is relevant.

After homogeneity of an image is estimated to determine the direction of least change in pixel data from a given camera pixel, color information for the given pixel may be interpolated in the direction of least change.

Figure 5A:
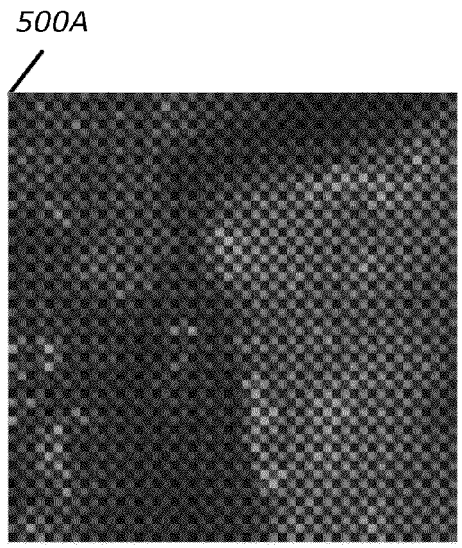
FIGS. 5A-5D illustrate how missing colors for a given camera pixel may be interpolated from neighboring camera pixels in the direction of least change.
Figure 5B:
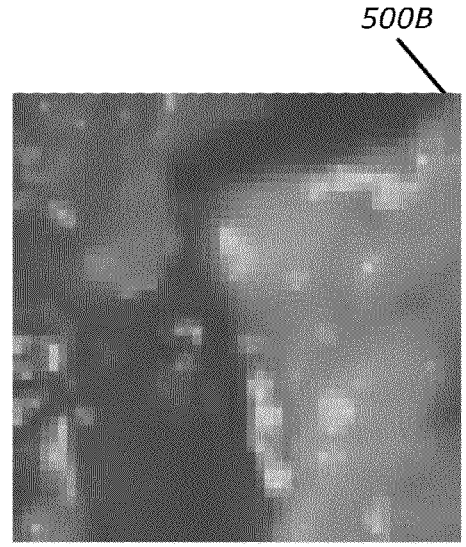

Referring now to FIG. 5A, a color mosaic image 500A is illustrated prior to interpolation and formation of a full color image. FIG. 5B illustrates a full color image 500B formed after interpolation of the camera pixels in the color mosaic image 500A. After interpolation, details of the contours in the full color image become apparent.

Figure 5C:
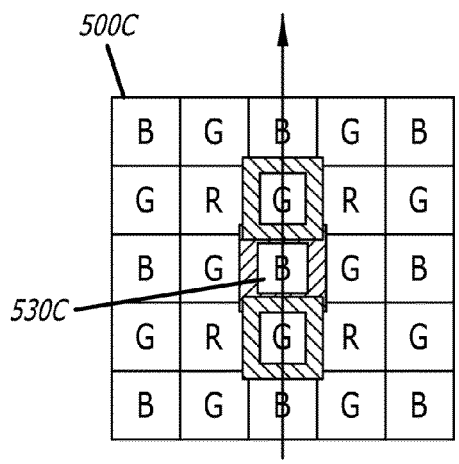

Reference is now made to FIG. 5C. In response to determining that the estimated homogeneity has the least amount of change in the vertical direction for a given camera pixel 530C, interpolation of the missing color information for the camera pixel 530C may be made using neighboring camera pixels in the vertical direction. If the camera pixel 530C is a blue camera pixel, the missing red and green color information for a full color pixel may be determined by interpolation of neighboring camera pixels. However in accordance with an aspect of the embodiments of the invention, correlation information between a pair of color channels is used over an array 500D of camera pixels to further improve spatial resolution of a full color image.

Figure 5D:
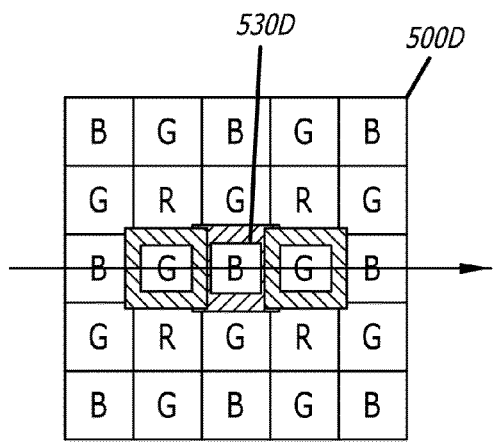

Reference is now made to FIG. 5D. In response to determining that the estimated homogeneity has the least amount of change in the horizontal direction for a given camera pixel 530D, the missing color information for the camera pixel 530D may be interpolated by using neighboring camera pixels in the horizontal direction. However in accordance with an aspect of the embodiments of the invention, correlation information between a pair of color channels is used over an array 500D of camera pixels to further improve spatial resolution of a full color image.

Demosaicing Algorithms

Figure 6A:
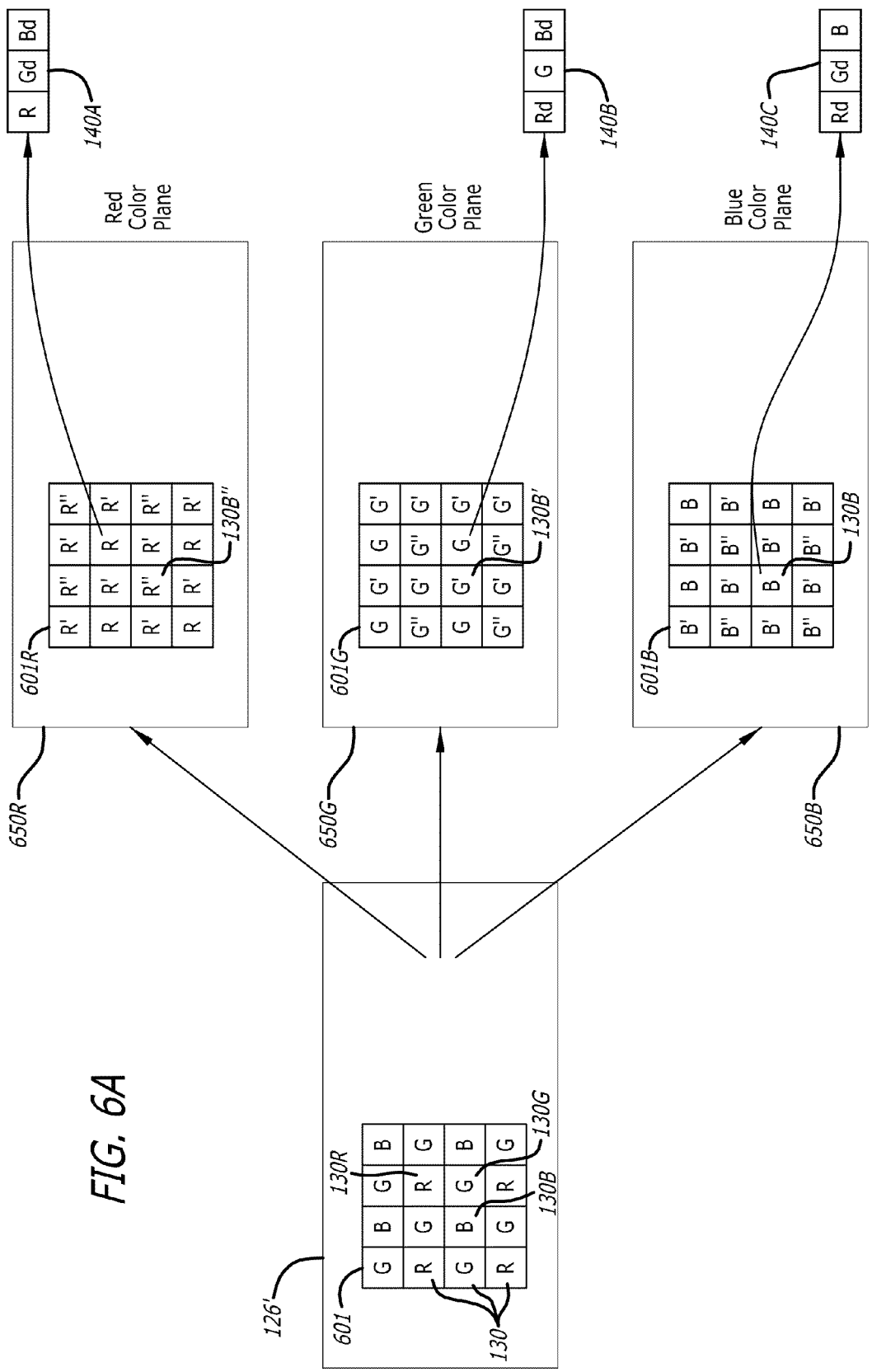
FIG. 6A illustrates a camera pixel array and the missing color information of each color plane for the camera pixels are estimated in order to form full color pixels.

Referring now to FIG. 6A, a color mosaic array 601 of single color camera pixels 130 within a frame 126' of M by N camera pixels is shown having a pattern generated by a color mosaic filter. The standard color mosaic pattern, known as a Bayer pattern, has spatially alternating red, green, and blue camera pixels with twice as many green pixels as red and blue pixels of known color information within the frame 126'. Regardless, to provide a full color image, the missing color information for each camera pixel needs to be determined for each array within a frame.

To form full color pixels, the missing color information associated with each single color camera pixel needs to be estimated. For example, consider the red camera pixels 130R with known red color information R. The missing red color information R' associated with green camera pixels and the missing red color information R" associated with blue camera pixels needs to be estimated to complete the array of red color information 601R within the red color plane 650R.

Similarly, green camera pixels 130G have known green color information G. The missing green color information G' associated with blue camera pixels and the missing green color information G" associated with red camera pixels need to be estimated to complete the array of green color information 601G in the green color plane 650G.

Similarly, blue camera pixels 130B have known blue color information B. The missing blue color information B' associated with green camera pixels and the missing blue color information B" associated with red camera pixels need to be estimated to complete the array of blue color information 601B in the blue color plane 650B.

Full color pixels are determined from the camera pixels in a demosaicing process. The estimates of the missing color information in the color planes are used with the known color information to determine spatial correlation between color channels. The spatial correlation may be used to generate a correlation map for each pixel location in the array of camera pixels.

The known color information of a given camera pixel may be used with the correlation information of the correlation map to demosaic a camera pixel into a full color camera pixel. For example, known red color information R 130R for a given camera pixel location within the array 601 may be joined with demosaic green color information Gd and demosaic blue color information Bd to form a full color pixel 140A.

Known green color information G 130G for another given camera pixel location within the array may be joined with demosaic red color information Rd and demosaic blue color information Bd to form the full color pixel 140B.

Known blue color information B 130B for another given camera pixel location within the array may be joined with the demosaic red color information Rd and the demosaic green color information Gd to form the full color pixel 140C.

Figure 6B:
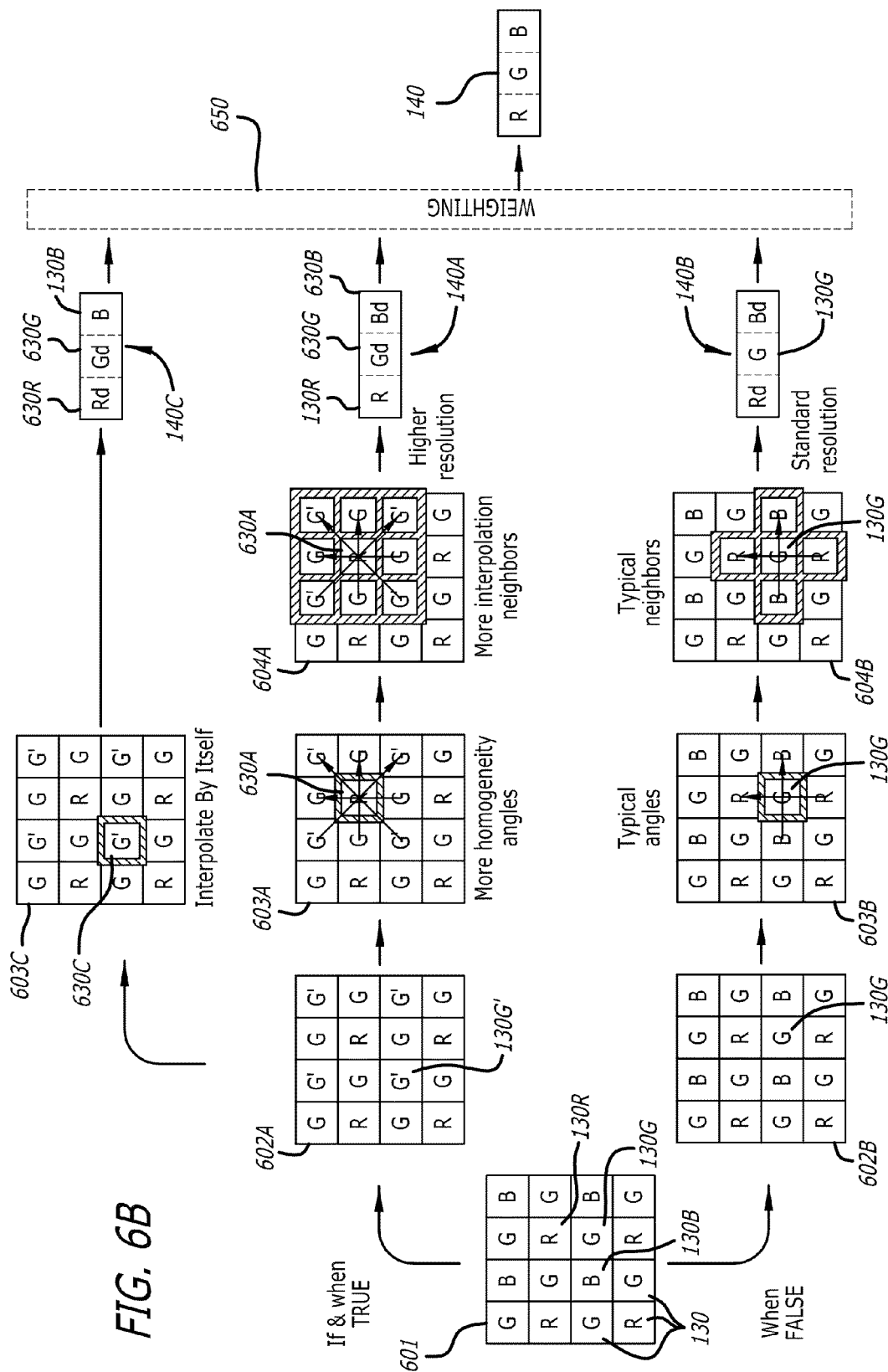
FIG. 6B illustrates the various methods of demosaicing that may occur to fill in the missing color information for a given camera pixel in order to form a full color pixel.

Referring now to FIGS. 6A-6B, various methods of demosaicing algorithms are illustrated that may be used to interpolate missing color information from a single color camera pixel 130 into a full color pixel 140. The demosaicing algorithm of the present invention can produce higher resolution images when two color channels are highly correlated, such as may be found in medical scenes (such as shown in FIG. 1E).

If a pair of color channels is highly correlated, the pair of color channels is proportional to each other by a constant scale factor. In this case, the missing color information associated with the highly correlated channel can be determined directly from the known color pixel value and a scale factor. That is, for a pixel in which color information for one color channel is known and for two color channels is unknown, and the known color channel information is highly correlated to color information in one of the two unknown color channels, then the color channel information for the highly correlated but unknown color channel can be determined directly from the known color channel information and a scale factor.

As a result, the demosaicing algorithm of the present invention can estimate one or more uncorrelated color channels with fewer pixel locations in order to fill in the remaining missing color information. At the same time, the demosaicing algorithm can produce more accurate estimates for missing pixel information because known pixel data of more surrounding camera pixels can be used to estimate the one or more uncorrelated color channels.

Moreover, if the correlation between two color channels turns out to be false or not highly correlated, the demosaicing algorithm can revert back to the typical lower-resolution demosaicing algorithms. Consequently, either full color pixel information of similar quality as produced by known interpolation methods can be achieved, or full color pixel information of higher quality can be achieved using the demosaicing algorithm of the present invention.

Within the color mosaic array 601 of the single color camera pixels 130, if it is determined that a pair of color channels is highly correlated, then methods of improving the resolution for a given camera pixel may be taken. However, if there is no correlation between color channels in the mosaic array 601 of camera pixels 130, then standard methods of interpolation may be used to estimate the missing color information. Furthermore, the standard method of interpolation may be combined with the high correlation method of interpolation to further improve resolution.

Arrays 602B-604B illustrate a typical method of interpolation for missing color information in a given camera pixel 130G to complete a full color camera pixel 140B. The standard color mosaic array is used in the arrays 602B-604B throughout this interpolation process. In the array 603B, homogeneity around the given camera pixel 130G is determined to determine the least changing direction of neighboring pixels. In the array 604B, the top and bottom neighboring pixels and/or the left and right neighboring pixels are used to interpolate the missing color information Rd,Bd in the camera pixel 130G to form the full color pixel 140B. Given the camera pixel 130G was green with know color information G, red color information Rd and blue color information Bd is added into the full color pixel 140B. The green color information G of the camera pixel 130G is passed onto the full camera pixel as the green color sub-pixel information.

If there is high correlation between a pair of color channels in the array 601 of camera pixels, the pair of color channels may be treated as having substantially proportional pixel data values by a fixed scale factor. In the case of high correlation, the pixel data of the camera pixels for the pair of color channels tends to spatially change together as was discussed herein with reference to FIGS. 2E and 2G. In which case, the known color information for the given camera pixel may be used itself to generate the missing color information of the highly correlated channel.

Arrays 601, 602A, and 603C illustrate one method of interpolation to determine missing color information if there is high correlation in the array of pixels 601 between a pair of color channels. For example, with medical images (see FIG. 1E) it is often common for the green and blue color channels to be substantially correlated. Accordingly, the blue color camera pixels B (e.g., camera pixel 130B) may be treated as green camera pixels G' (e.g., camera pixel 130G') as shown in the array 602A, if there is substantially high correlation in the pixel data between the green and blue color channels for the camera pixels. The standard color mosaic array 601 may be transformed into an effective array 602A of camera pixels. In response to the substantially high correlation in pixel data in the array 601 of camera pixels between any pair of color channels, a given camera pixel 130 may use its own base single color information to generate the remaining missing color information for the corresponding full color pixel 140.

The effective array 602A of camera pixels, illustrates one or more color camera pixels 130 being interpolated by themselves with their own underlying known color information to determine the missing color information of its substantially correlated channel. In response to the substantial high correlation between a pair of color channels, the known color information for a given camera pixel 130 is used to generate the unknown color information of its substantially correlated channel. With a blue camera pixel B 130B for example, the missing green pixel data G' is derived from the known blue pixel data of the blue camera pixel. The missing blue pixel data B' of a green camera pixel 130G is derived from the known green pixel data G of the green camera pixel. With all the missing pixel data of the highly correlated channels determined by the known pixel data of its correlated channel, any remaining uncorrelated channels, for example the red camera pixel 130R, can use more neighboring pixels to enhance standard demosaicing algorithms.

The pixel data for the different colors in a multi-channel or full color pixel 140 may be referred to as sub-pixels. For example, the full color pixel 140C includes a red color sub-pixel Rd 630R, a green color sub-pixel Gd 630G, and a blue color sub-pixel B 130B. Various widths of bits may be used to represent each color. The sub-pixel data may be used as an index into a color map or color look up table of a color palette for each color channel. For example, 8 bits per sub-pixel allows a level between zero and two hundred fifty-five to select a color palette. In a true color format, the 8 bits per sub-pixel allows a color level between zero and two hundred fifty-five of each primary color red, green, and blue. A fourth sub-pixel (see sub-pixel 140X in FIG. 2B, for example) may be used such as for a yellow color, levels of transparency or shading, and/or other data to represent three dimensions.

In the full color pixel 140C, the base information or known sub-pixel data (KC) of the blue color B of the camera pixel 130B is joined together with the estimated sub-pixel data (EC) or interpolated the red color sub-pixel 630R and the estimated sub-pixel data (EC) or interpolated green color sub-pixel 630G. Not only may a given camera pixel use its base or known pixel information to generate the missing color information, but neighboring camera pixels may also be used to further improve the resolution of interpolating a frame of given camera pixels into a frame of full color pixels for a full color image.

The effective color mosaic array 602A illustrates that the blue and green color channels of data for blue color sub-pixels and green color sub-pixels, for example, are highly correlated. The data of the missing green color sub-pixel information are estimated by being proportional by a factor of the data of the blue sub-pixel. For example, in array 602A, the missing data G' for the green color sub-pixel 103B' can be generated from the known blue color data of the blue color sub-pixel 103B. If instead the red color channel was highly correlated to the blue color subchannel, missing information R" for a red color sub-pixel 130B" can be generated from the known blue color data B of the blue color sub-pixel 103B.

The effective color mosaic arrays 603A and 604A illustrate using additional neighboring camera pixels to better interpolate the missing color information. As mentioned previously, the standard array 601 may be transformed into an effective color mosaic array 602A of camera pixels if there is a substantial correlation between a pair of color channels in the array of camera pixels. In the color mosaic array 603A, additional angles of neighboring camera pixels may be used to detect homogeneity. Not only may the horizontal and vertical camera pixels (horizontal—east and west camera pixels, vertical—north and south camera pixels) be utilized to detect homogeneity, but the camera pixels along diagonal lines (diagonal angles not ninety degree angles; e.g., forty five degree angles) where the neighboring diagonal or corner pixels (north-west, north-east, south-west, south-east camera pixels) lie may be utilized to detect homogeneity. The neighboring or adjacent camera pixels of the given camera pixel 630A may be used to further interpolate the missing color information along with the known color information of the given camera pixel. With a high degree of correlation between a pair of color channels, the neighboring pixels along the diagonal axes may have the least change in pixel level and be used to further interpolate the missing color information, along with the known color information in the given camera pixel, to generate the full color pixel.

As mentioned previously, homogeneity is often used to detect the least amount of change between adjacent neighboring pixels. With the neighboring diagonal pixels along the diagonal angles at the corners being used, there is a greater number of potential interpolation neighboring camera pixels to choose from.

The mosaic array 604A illustrates interpolation along not only the horizontal and vertical axis, but also along the diagonal angles to interpolate the missing color information from that of the given camera pixel. For example, in FIG. 6B the camera pixel 130R is shown to be a red camera pixel. In the case of a red camera pixel 130R, the red color information R is known and is transferred to be the red sub-pixel in the full color pixel 140A. By interpolation, the missing green color information Gd is generated and stored as the green sub-pixel 630G and missing blue color information Bd is generated and stored as the blue sub-pixel 630B in the full color pixel 140A.

Each of the interpolation methods may be selectively used to form a full color pixel or the results of each method may be combined together to try and improve the resolution in the full color pixel. An optional weighting mechanism 650 illustrated in FIG. 6B may be utilized to selectively combine results of the one or more interpolation methods together in response to detection of a substantial correlation in a pair of color channels in the array 601 of camera pixels 130.

Figure 7A:
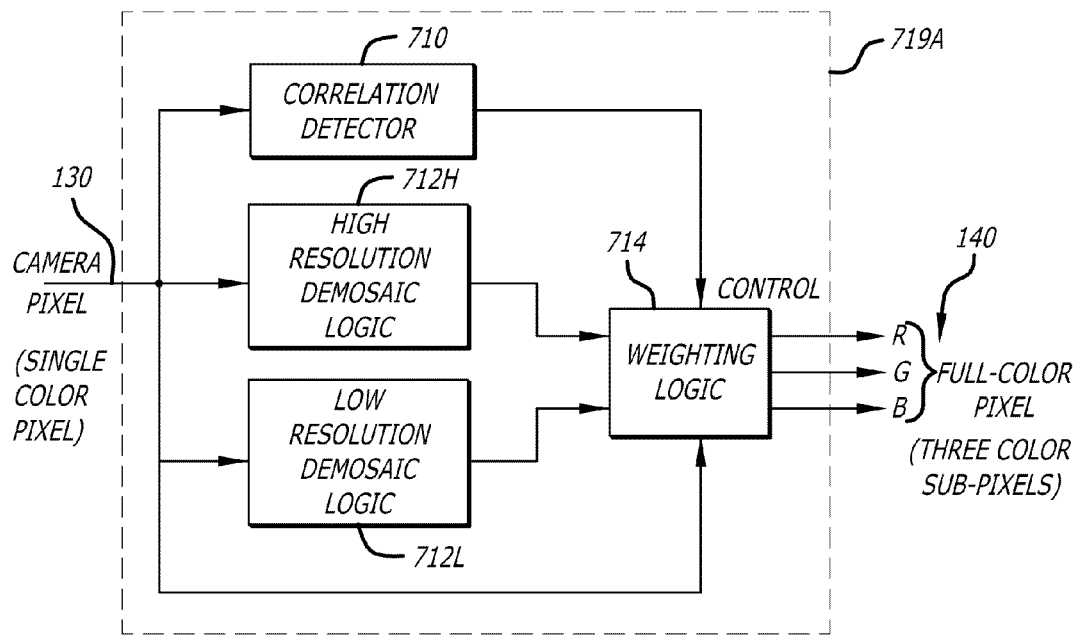
FIG. 7A is a block diagram of a demosaicing image processor employing a correlation demosaicing algorithm.
Figure 7B:
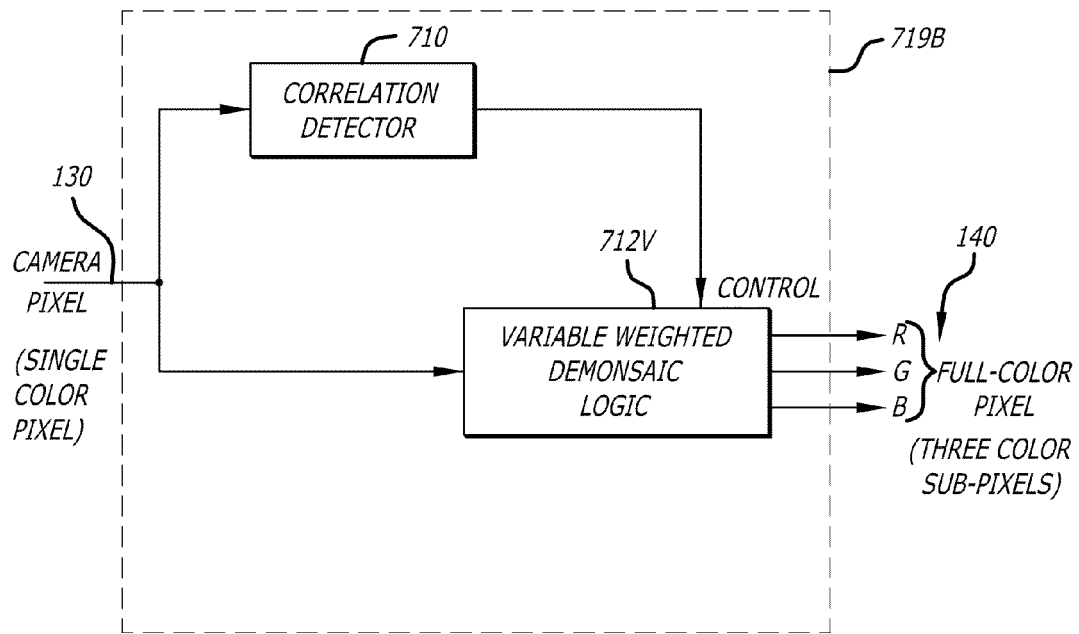
FIG. 7B is a block diagram of a demosaicing image processor employing a correlation demosaicing algorithm.

Referring now to FIGS. 7A-7B, alternate embodiments of demosaic logic 719A-719B is respectively illustrated. The demosaic logic 719A-719B may be an instance of the demosaic logic 119A and 119B shown in FIG. 1A and FIG. 1C respectively.

In FIG. 7A, the demosaic logic 719A includes a correlation detector 710, high-resolution demosaic logic 712H, low-resolution demosaic logic 712L, and weighting logic 714 coupled together as shown.

Each of the correlation detector 710, high-resolution demosaic logic 712H, low-resolution demosaic logic 712L, and weighting logic 714 process each camera pixel 130 within each frame of the captured image. The correlation detector 710 selectively operates over constant or varying array sizes (variable M by variable N) of camera pixels to determine if a pair of color channels is substantially correlated within the array. The correlation detector 710, the high-resolution demosaic logic 712H and the low-resolution demosaic logic 712L can operate in parallel. However, the data flow may be buffered by data buffers in order to synchronize the control signal flow and the pixel data signal flow at the weighting logic 714 to properly generate the full color pixel 140 output there-from.

The correlation detector 710 receives an array of camera pixels 130 and detects whether or not there is at least one pair of color channels that are substantially correlated together. The correlation detector 710 generates a control output indicting the level of correlation in the array between the color channels and couples it into the weighting logic 714. The control output from the correlation detector 710 indicates substantial correlation between a pair of color channels so that the weighting logic can choose to weight and use the pixel data output from the high-resolution logic over the pixel data output from the low-resolution demosaic logic.

The high-resolution demosaic logic 712H and the low-resolution demosaic logic 712L each generate the missing color information in the camera pixel 130 for the corresponding full color pixel 140. The high-resolution demosaic logic 712H performs the high-resolution demosaicing algorithm and interpolation methods shown in FIG. 6B and described herein to generate the full color pixel 140A,140C and provide a higher resolution full color image output. The low-resolution demosaic logic 712L performs the low-resolution demosaicing algorithm and interpolation methods shown in FIG. 6B and described herein in generating the full color pixel 140B and a full color image output. The missing color information output from the low-resolution demosaic logic 712L is a function of neighboring camera pixel values and homogeneity (direction of least change) in the selection of the neighboring camera pixel values for interpolation. The missing color information output from the high-resolution demosaic logic 712H is a function of the known color information of the given camera pixel. Neighboring camera pixel values and homogeneity (direction of least change) may also be used in the generation of the missing color information output from the high-resolution demosaic logic 712H.

The weighting logic 714 receives the known color information from the current camera pixel and multiplexes it out to the appropriate sub-pixel within the full color pixel 140. For example, if the camera pixel 130 is a blue camera pixel, the weighting logic 714 multiplexes the camera pixel data into the blue sub-pixel of the full color pixel 140. Furthermore, the weighting logic 714 may utilize the known color information of the camera pixel 130 in the generation of the missing color information (missing sub-pixel information) for the full color pixel 140.

In response to the level of correlation, the weighting logic 714 may implement weighting algorithms to weight high-resolution data HRD from the high-resolution demosaic logic 712H, low-resolution data LRD from the low-resolution demosaic logic 712L, and the known color pixel data KC of the camera pixel 130 in the generation of missing color information ($MC_1$ and $MC_2$) in the full color pixel 140. For example, weights $W_1$, $W_2$, $W_3$ may be generated for first missing color information $MC_1$ and weights $W_4$, $W_5$, $W_6$ may be generated for second missing color information $MC_2$ in the following weighting equations:

$$MC_1 = W_1 KC + W_2 HRD + W_3 LRD.$$

$$MC_2 = W_4 KC + W_5 HRD + W_6 LRD.$$

The weights in the missing color equations may be discrete numeric values that select the mixture of the three pieces of information (KC, HRD, LRD) that is available. Alternatively, in response to the level of correlation detected by the correlation detector 710, one or more variables may be used to generate the missing color pixel information from the known pixel data of the camera pixel 130 and the pixel data of neighboring camera pixels.

Referring now to FIG. 7B, an alternate embodiment of demosaic logic 719B is illustrated. The demosaic logic 719B includes the correlation detector 710 and a variable weighted demosaic logic 712V coupled together as shown. The correlation detector 710 and the variable weighted demosaic logic 712V both receive the known pixel data of the camera pixel 130. The variable weighted demosaic logic performs the function of the various demosaic and interpolation methods shown in FIG. 6 in the generation of an improved resolution full color pixel 140. The correlation detector 710 detects a level of correlation between at least one or more pairs of color channels in a color mosaic array of camera pixels 130. The mosaic array may be made up of M by N camera pixels 130 where M and N may be variables. The level of correlation detected by the correlation detector 710 is coupled into the variable weighted demosaic logic 712V.

A control input of the variable weighted demosaic logic 712V receives the level of correlation from the correlation detector. In response to the level correlation, the variable weighted demosaic logic 712V generates the missing color information $MC_1$, MC2 for the full color pixel 140 from the known color information KC of the camera pixel 130 in response to a variable weighting $W_{v1}$, $W_{v2}$. The following equations for the first and second missing color information are representative.

$$MC_1 = W_{v1} KC.$$

$$MC_2 = W_{v2} KC.$$

The known color information from the camera pixel 130 is coupled into the variable weighting detector 712V and the correlation detector 710. The known color information from the camera pixel 130 is passed onto the respective color sub-pixel in the full color pixel 140 by weighting it to be 100% of the known color information. For example if the camera pixel is a green camera pixel 130G, the variable weighted demosaic logic may generate 100% weight and merely pass the known green color information of the camera pixel 130G into the green sub-pixel of the full color pixel 140. The missing sub-pixel color information is generated from the known color information in the camera pixel 130 and selectively weighted by the variable weighted demosaic logic in response to the level of correlation detected by the correlation detector.

Demosaicing Methods

Figure 8:
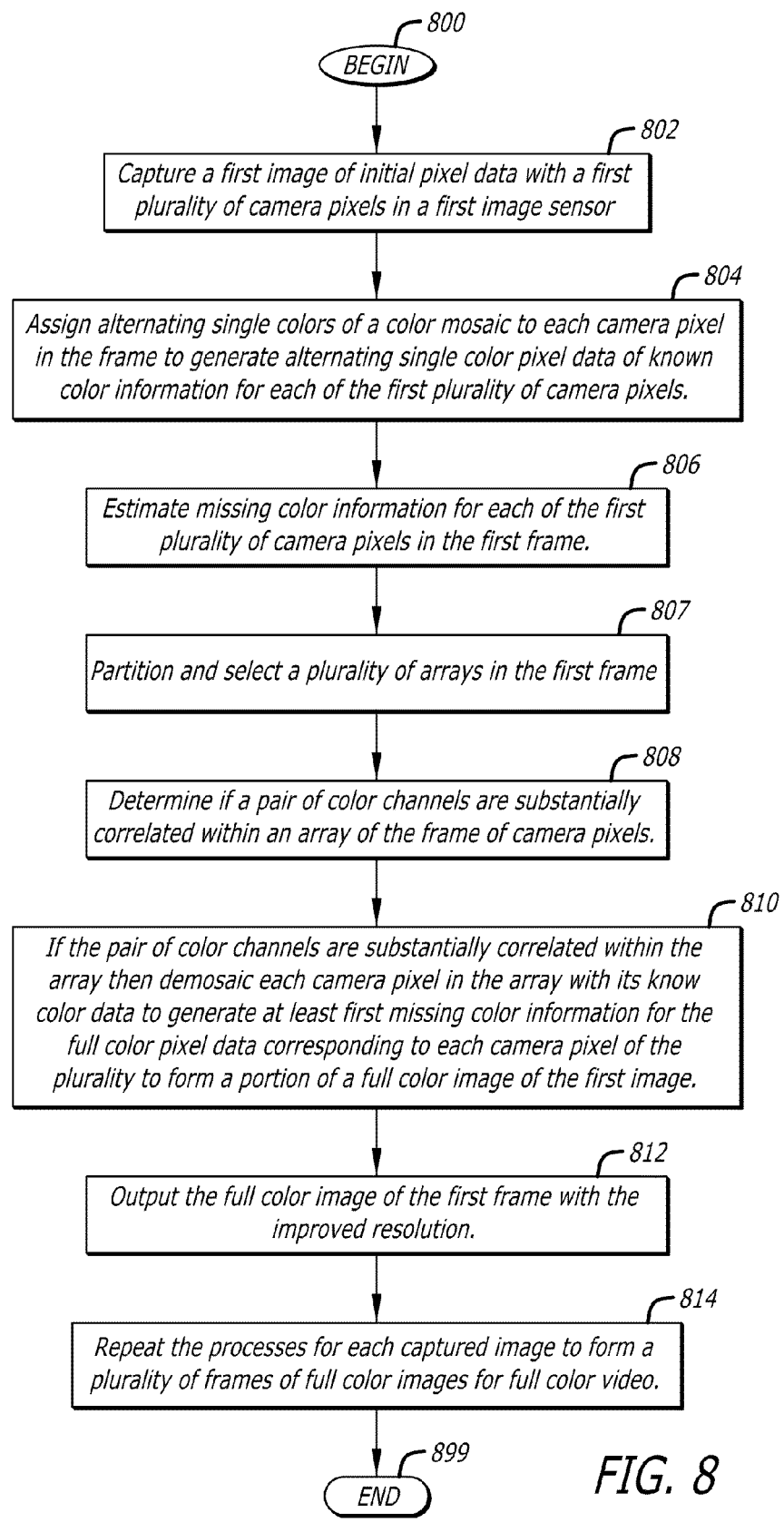
FIGS. 8-10 are flow chart diagrams illustrating demosaicing processes in accordance with embodiments of the invention.

Referring now to FIG. 8, a method of image processing is now described that begins at process block 800. One or more of the process elements may be performed with a processor. The process goes to process block 802.

At process block 802, a first image (also referred to as a first captured image) is captured with at least a first image sensor. The first captured image includes a first frame of initial pixel data captured by a first plurality of camera pixels. The first captured image may be a medical image captured from a surgical site within a patient. A surgical site may include tissue of the patient such that the first captured image includes a plurality of pixel data representing the tissue of the patient. A surgical site may further include one or more of robotic surgical tools and body fluids. In which case, the first captured image includes a plurality of pixel data representing the one or more of robotic surgical tools and the body fluids. After capturing the first image, the process then goes to process block 804.

At process block 804, a color mosaic of color information is assigned to the initial pixel data to generate alternating single-color pixel data of known color information for each of the first plurality of camera pixels. At least two-color channels are formed by at least two colors (e.g., red, green, blue, and/or yellow) of sub-pixel data within at least two-color planes (e.g., red, green, blue, and/or yellow color planes). A color filter array aligned with the sensor assigns the mosaic of color information to the initial grey-scale pixel data of each of the plurality of camera pixels. The process then goes to process block 806.

At process block 806, missing color information is estimated for each of the first plurality of camera pixels in the first frame. The missing color information may be estimated by averaging known color information of respective neighboring camera pixels associated with the same respective color. The estimates for the missing color information may be used to form a correlation map for the frame of camera pixels. The process then goes to process block 807.

At process block 807, the first frame may be selectively partitioned into a plurality of arrays. The selection and partitioning of the first frame into a plurality of arrays may be in response to a correlation map. The process then goes to process block 808.

At process block 808, for each array of a plurality of arrays of camera pixels in the first frame, correlation information is generated. The correlation information may be annotated to the correlation map. The correlation information may used to determine if a pair of at least two-color channels are substantially correlated within each array in response to the known color information and the estimated color information for each camera pixel in the array.

A pair of color channels are highly correlated within the array if, a change in level of color information (e.g., intensity) for the pair of color channels is substantially similar (e.g., within 90% to 100%) from camera pixel to camera pixel in the array. The process goes to process block 810.

At process block 810, a determination is made if a pair of color channels is substantially correlated within an array. If a pair of color channels is substantially correlated within an array, then each camera pixel in the array can be demosaiced in response to its single-color pixel data and the correlation information. Camera pixels are demosaiced to generate full color pixel data for each camera pixel within the array and form a portion of a full color image of the captured image. With a high degree of correlation between at least a pair of color channels, the single-color pixel data of a given camera pixel may be used alone with the correlation information to demosaic the given camera pixel into a full color pixel. A missing color of the highly correlated color channel for a given camera pixel is interpolated by scaling the single-color pixel data of the given camera pixel in response to the correlation. The scaling factor may vary depending upon the level of correlation and location of the pixel within the image frame.

Spatial resolution of a missing data for a sub-pixel may be further improved by interpolating the known camera pixel data for the given location with the neighboring pixel data.

If other color channels are not highly correlated within the array, standard interpolation methods may be used to demosaic the camera pixels to generate full color pixel data. Other missing color of the given camera pixel, one that may not be highly correlated, may be determined by interpolating the neighboring pixel data of the given camera pixel. The neighboring camera pixels may include adjacent on-axis camera pixels along vertical and horizontal axes and/or adjacent off-axis camera pixels along left and right diagonal axes. In one embodiment of the invention, the estimated color may be used to form one or more sub-pixel data of the full color pixel. Similarly if in the array of camera pixels, no pair of color channels are substantially correlated, each camera pixel in the array may be demosaiced with on-axis adjacent camera pixels to generate full color pixel data for the given camera pixel but with lower resolution.

Process block 810 may be repeated for each array of camera pixels in the frame to complete the full color image of the captured image. The process then goes to process block 812.

At process block 812, the full color image of the first frame with improved resolution is output for display. If the captured image and full color image are for still images, the process may go to process block 899 and end. If the captured image and the full color image are to be repeated for video purposes, the process goes to process block 814.

At process block 814, the processes may be repeated for each of a plurality of captured images to form a plurality of frames of full color images. The plurality of frames of full color images may be output to provide full color video with improved resolution. Upon completion of capturing video or still images, the process may go to block 899.

At process block 899, the process ends.

Figure 9:
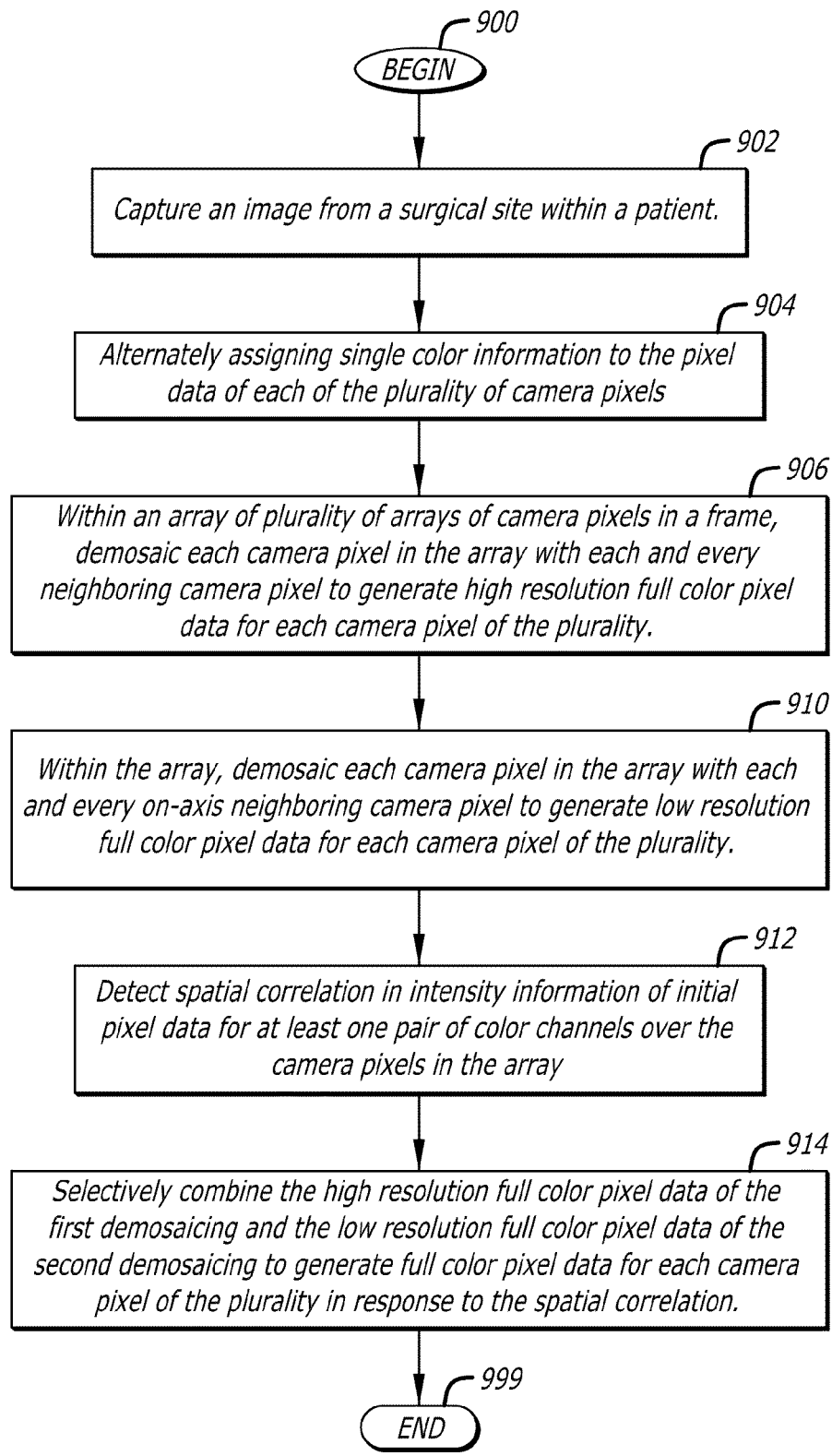

Referring now to FIGS. 7A and 9, a method for a minimally invasive surgical system is now described starting from a beginning process block 900 in the process. The process goes to process block 902.

At process block 902, an image from a surgical site within a patient is captured. The captured image includes a frame of pixel data captured by a plurality of camera pixels. The process then goes to process block 904.

At process block 904, single color information is alternatively assigned to the pixel data of each of the plurality of camera pixels to form a color mosaic in the frame of initial pixel data. A color mosaic of alternating single color information in a frame of pixel data is shown, for example, by the frame 126' in FIG. 2A. In one row, green and blue color information alternates from camera pixel to camera pixel. In another row, red and green color information alternates from camera pixel to camera pixel. The single color information may be alternatively assigned to the camera pixels by a color mosaic filter. The process then goes to block 906.

At process block 906, within an array of a plurality of arrays of camera pixels in a frame, each camera pixel in the array is demosaiced with itself by the high-resolution demosaicing logic 712H to generate high-resolution full color pixel data for each camera pixel. Each camera pixel in the array may be further demosaiced by high-resolution demosaicing logic 712H with each and every neighboring camera pixel to generate the high-resolution full color pixel data for each camera pixel. The process then goes to block 908.

At process block 908, each camera pixel in the array is demosaiced by the low-resolution demosaicing logic 712L with each and every on-axis neighboring camera pixel to generate low-resolution full color pixel data for each camera pixel. The process then goes to block 910.

At process block 910, a correlation detector 710 is used to detect spatial correlation in intensity information of the initial pixel data for a pair of color channels (e.g., red and green, red and blue, blue and green) over the camera pixels in the array. To ease detection, a correlation map of correlation information may be generated for at least one pair of color channels for the plurality of camera pixels. The process then goes to process block 912.

At process block 912, the high-resolution full color pixel data generated by the high-resolution demosaicing logic 712H and the high-resolution full color pixel data generated by the low-resolution demosaicing logic 712L is selectively combined to generate the full color pixel data for each camera pixel in the array in response to the spatial correlation detected by the correlation detector 710. The full color pixel data of the demosaicing processes may be selectively combined together by weighting the low-resolution full color pixel data and the high-resolution full color pixel data to generate the full color pixel data for each camera pixel. Alternatively, the full color pixel data of the demosaicing processes may be selectively combined together by switching between the low-resolution full color pixel data and the high-resolution full color pixel data to generate the full color pixel data for each camera pixel.

The method may repeat the processes as needed to complete the demosaicing of a frame of camera pixels. The process may also be repeated over a plurality of frames of camera pixels to demosaic the camera pixels into full color pixels and provide full color video. Two parallel process may be executed one for left images and another for right images to generate full color stereo video. The images may be output and displayed by one or more display devices. Otherwise, the process may go to process block 999.

At process block 999, the process ends.

Figure 10:
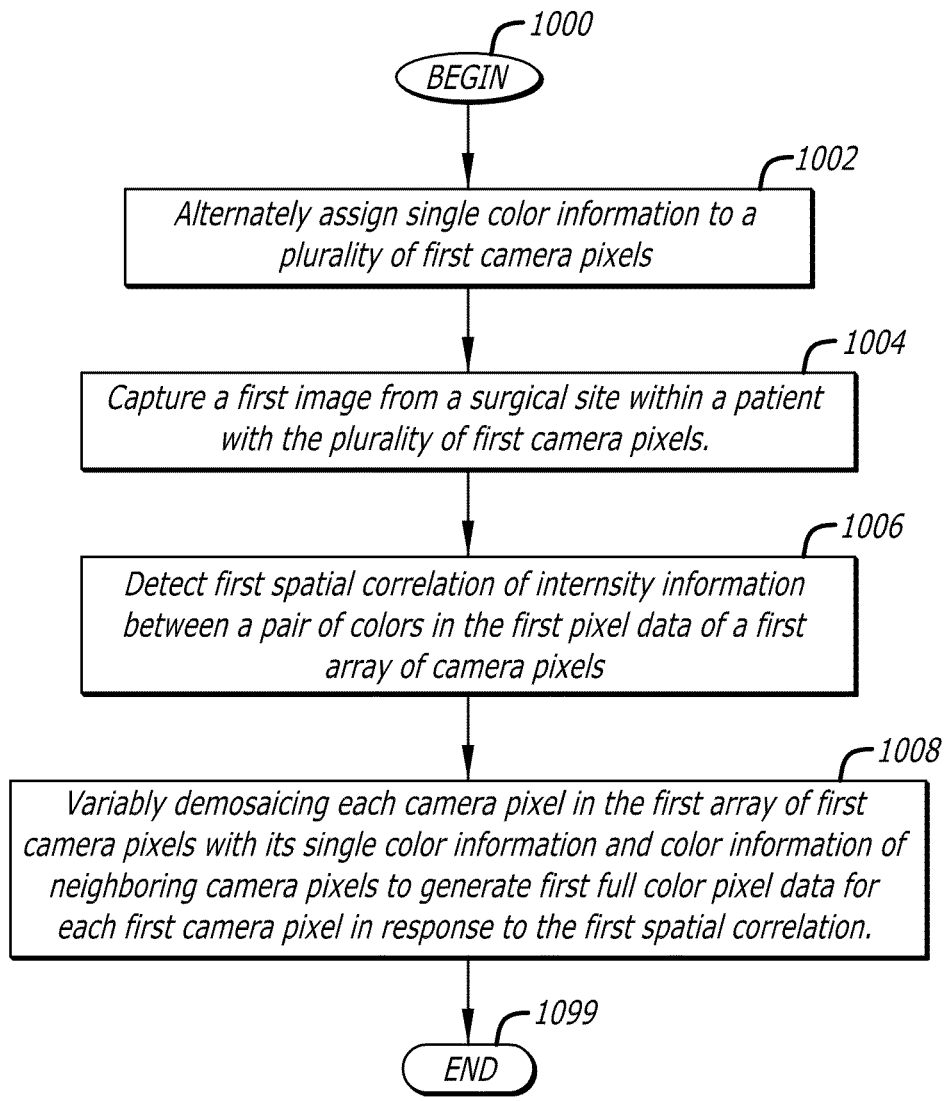

Referring now to FIGS. 7B and 10, a method for a minimally invasive surgical system is now described starting from a beginning point 1000 in the process. The process goes to process block 1002.

At process block 1002, single color information is alternately assigned to a plurality of camera pixels. The assignment forms a color mosaic for a frame of M by N camera pixels. The process goes to process block 1004.

At process block 1004, an image is captured from a surgical site within a patient with the plurality of camera pixels. The image includes pixel data of the plurality of camera pixels. The process then goes to process block 1006.

At process block 1006, a correlation detector 710 detects the spatial correlation of intensity information between at least one pair of colors in the pixel data of an array of camera pixels. The process goes to process block 1008.

At process block 1008, each camera pixel in the array of camera pixels is variably demosaiced with its single color information and color information of neighboring camera pixels to generate full color pixel data for each camera pixel in response to the spatial correlation.

The method may repeat the processes as needed to complete the demosaicing of a frame of camera pixels. The process may also be repeated over a plurality of frames of camera pixels to demosaic the camera pixels into full color pixels and provide full color video.

Two parallel processes may also be executed, a first process (process blocks 1002-1008) for left images and a second process for right images, to generate full color stereo video. The second process may include alternately assigning single color information to a plurality of second camera pixels. This assignment forms a color mosaic for a second frame of M by N camera pixels. A second image is captured from the surgical site within the patient with the plurality of camera pixels. The second image includes second pixel data of the plurality of camera pixels. The correlation detector detects spatial correlation of intensity information between at least one pair of colors in the pixel data of a second array of camera pixels. Each camera pixel in the second array of camera pixels is variably demosaiced with its single color information and color information of neighboring camera pixels to generate full color pixel data for each camera pixel in response to the spatial correlation.

The images may be output and displayed by one or more output devices. For example, left pixel data may be output and displayed on a left display output device of a stereo display device and right pixel data may be output and displayed on a right display output device of the stereo display device.

Otherwise if the processing of images is completed, the process goes to process block 1099. At process block 1099, the process ends.

CONCLUSION

If a pair of color channels are substantially correlated within a color mosaic image captured by a single-chip color camera, a high-resolution demosaicing algorithm can treat the pair of color channels to be proportional to each other by a scale factor when demosaicing the image into a full color image of full color pixels. When capturing medical images (see FIG. 1E), there is a high probability that the pixel data of the green and blue color channels of camera pixels will be substantially spatially correlated over pixel locations. With substantial correlation between a pair of channels, the pair of channels can be effectively treated the same having similar pixel data at each camera pixel location within an array and can increase the resolution of the resultant demosaiced full color image. The embodiments of the invention can produce higher resolution images from a typical single-chip color camera. The embodiments of the invention also allow for graceful transition from a higher resolution demosaicing algorithm to lower resolution demosaicing algorithms, if the correlation level between a pair of color channels (e.g., blue and green color channels) drops in a scene of an image and they are no longer highly correlated.

One or more elements of the embodiments of the invention may be implemented in software so that one or more tasks may be automatically performed with a machine, such as a processor. When implemented in software, the elements of the embodiments of the invention are essentially the program instructions or code segments to perform the one or more tasks of the methods disclosed herein. For example, a machine readable media may have stored thereon instructions that when executed by a machine causes the machine to automatically perform operations including capturing a first image from a surgical site within a patient, the first image including first pixel data of a first plurality of first camera pixels; assigning single color information to the first pixel data of each of the first plurality of camera pixels; detecting first spatial correlation of intensity information between a pair of colors in the first pixel data of a first array of camera pixels; and variably demosaicing each camera pixel in the first array of camera pixels with neighboring camera pixels to generate first full color pixel data for each first camera pixel in response to the first spatial correlation.

The program instructions or code segments can be stored in a processor readable medium (e.g., memory 123) for execution by a processor, such as processor 120 shown in FIG. 1A. The processor readable medium may include any medium that can store information, such as a storage device for example. Examples of a storage device include an electronic circuit, a semiconductor memory device, a read only memory (ROM), a flash memory, a programmable read only memory (PROM), a floppy diskette, a compact disk (CD-ROM), an optical disk, a hard disk, etc. The program instructions or code segments may be downloaded via computer networks such as the Internet, Intranet, etc.

While this specification includes many specifics, these should not be construed as limitations on the scope of the disclosure or of what may be claimed, but rather as descriptions of features specific to particular implementations of the disclosure. For example, primary colors of red, green, and blue (an additive color system) are described as being base camera pixel information and sub-pixel information of a full color pixel. However, the embodiments of the invention may be employed with pixels having different type of sub-pixel information such as cyan, magenta, and yellow (CMY), a subtractive color system; hue (color), saturation (chroma), and value (brightness) (HSV), a variable color property system; or YUV and its variants, for example. Furthermore, certain features that are described in this specification in the context of separate implementations may also be implemented in combination in a single implementation. Conversely, various features that are described in the context of a single implementation may also be implemented in multiple implementations, separately or in sub-combination. Moreover, although features may be described above as acting in certain combinations and even initially claimed as such, one or more features from a claimed combination may in some cases be excised from the combination, and the claimed combination may be directed to a sub-combination or variations of a sub-combination. The claimed invention is limited only by patented claims that follow below.

What is claimed is:

1. A method of image processing comprising:

receiving, by a processor, a frame of pixel data captured by a plurality of camera pixels, the pixel data including alternating single-color pixel data of known color information for each of the plurality of camera pixels of the frame to form at least two color channels, the frame of pixel data representing a captured image;

with the processor, estimating missing color information for each of the plurality of camera pixels in the frame to obtain estimated color information for the missing color information;

for each array of a plurality of arrays, each array of the plurality of arrays including camera pixels of the plurality of camera pixels in the frame, generating correlation information to determine if a pair of the at least two color channels are substantially correlated in response to the known color information and the estimated color information; and demosaicing, by the processor, each camera pixel of an array of the plurality of arrays, wherein if within an array of the plurality of arrays, a pair of color channels are substantially correlated then the demosaicing each camera pixel further comprises:

demosaicing each camera pixel in a first color channel of the pair of color channels in response to single-color pixel data of the first color channel of the pair of color channels and the correlation information to generate color pixel data for a camera pixel in a second color channel, the demosaicing each camera pixel in a first color channel of the pair of color channels comprising interpolating a first missing color pixel of the second color channel for a given pixel in the first color channel by scaling the single-color pixel data of the given pixel in response to the correlation information.

2. The method of claim 1, further comprising forming a correlation map for the frame of camera pixels, the correlation map including the estimated color information; and wherein the estimating missing color information further comprises:
 averaging known color information of respective neighboring camera pixels associated with the same respective color.

3. The method of claim 2, further comprising:
 selecting the plurality of arrays in the frame in response to the correlation map; and
 outputting a full color image of the captured image.

4. The method of claim 1, wherein the alternating single-color pixel data of known color information is based on a mosaic of a color filter array.

5. The method of claim 1, the demosaicing each camera pixel of an array of the plurality of arrays further comprising:
 demosaicing a selected camera pixel of the array of the plurality of arrays using information from each and every neighboring camera pixel adjacent to the selected camera pixel.

6. The method of claim 5, wherein the neighboring camera pixels include northwest, southwest, northeast, and southeast adjacent camera pixels.

7. The method of claim 1, wherein the single-color pixel data of a given camera pixel is used alone with the correlation information to demosaic the given camera pixel into a full color pixel.

8. The method of claim 1, wherein a pair of color channels is substantially correlated within the array if a change in level of color information for the pair of color channels is substantially similar from camera pixel to camera pixel in the array.

9. The method of claim 1, wherein the demosaicing of each camera pixel of an array of the plurality of arrays further includes:
 interpolating the neighboring pixel data to determine a second missing color pixel of the given camera pixel.

10. The method of claim 1, wherein the demosaicing of each camera pixel of an array of the plurality of arrays further includes:
 estimating homogeneity of a given camera pixel with each neighboring camera pixel, and
 further interpolating the given camera pixel with neighboring pixel data in response to the homogeneity to determine the first missing color pixel of the given camera pixel.

11. The method of claim 10, wherein each neighboring camera-pixel includes adjacent on-axis camera pixels along vertical and horizontal axes and adjacent off-axis camera pixels along left and right diagonal axes.

12. The method of claim 8, wherein in the array of the plurality of arrays, no pair of color channels is substantially correlated such that the demosaicing each of an array of the plurality of arrays further comprises:
 demosaicing each camera pixel in the array with on-axis adjacent camera pixels to generate lower resolution full color pixel data for the given camera pixel.

13. The method of claim 1, wherein the captured image is a medical image captured from a surgical site within a patient.

14. The method of claim 13, wherein the surgical site includes tissue of the patient; and wherein the captured image includes a plurality of pixel data representing the tissue of the patient.

15. A method for a surgical system, the method comprising:
 receiving, by a processor, a frame of pixel data captured by a plurality of camera pixels, the frame of pixel data including data for each of the plurality of camera pixels, and the data for each of the plurality of camera pixels including single color information for one of a plurality of color channels;
 in an array of camera pixels of the plurality of camera pixels in the frame, the array being one array in a plurality of arrays,
  estimating, by the processor, spatial correlation in intensity information for each color channel of the plurality of color channels relative to the other color channels of the plurality of color channels over all the camera pixels of the plurality in the array,
  first demosaicing, by the processor, each camera pixel in the array by using the estimated spatial correlation to generate high-resolution full color pixel data for each camera pixel in the array,
  second demosaicing, by the processor, each camera pixel in the array with neighboring camera pixels in the array to generate low-resolution full color pixel data for each camera pixel of the plurality in the array, and
  selectively combining, by the processor for each camera pixel in the array, the single color information of a camera pixel in the array, the high-resolution full color pixel data of the camera pixel, and the low-resolution full color pixel data of the camera pixel to generate full color pixel data for the camera pixel in the array, the selectively combining being in response to the estimated spatial correlation.

16. The method of claim 15, wherein the selectively combining comprises selectively weighting the low-resolution full color pixel data and the high-resolution full color pixel data to generate the full color pixel data for each camera pixel in the array.

17. The method of claim 15, wherein the selectively combining comprises switching between the low-resolution full color pixel data and the high-resolution full color pixel data to generate the full color pixel data for each camera pixel in the array.

18. The method of claim 15, further comprising: prior to estimating the spatial correlation in intensity information, generating a correlation map of correlation information of at least one pair of color channels of the plurality of color channels for the plurality of camera pixels in the frame, wherein the correlation map includes estimated missing color information for each of the plurality of camera pixels in the frame.

19. A method for a surgical system, the method comprising:
 receiving, by a processor, a first frame of pixel data captured by a first plurality of camera pixels, the first frame of pixel data including data for each of the first plurality of camera pixels, the first frame of pixel data representing a first image of a surgical site, and the data for each of the first plurality of camera pixels including single color information for one of a plurality of color channels;
 detecting, by the processor, first spatial correlation of intensity information between a pair of the plurality of color channels in the first pixel data of a first array of the first plurality of camera pixels; and variably demosaicing, by the processor in response to the first spatial correlation, each camera pixel in the first array of the first plurality of camera pixels by scaling single color information of a camera pixel in the first array based on the first spatial correlation to generate first full color pixel data for the camera pixel in the first array of the first plurality of camera pixel.

20. The method of claim 19, further comprising:

receiving, by the processor, a second frame of pixel data captured by a second plurality of camera pixels, the second frame of pixel data including data for each of the second plurality of camera pixels, the second frame of pixel data representing a second image of a surgical site and the data for each of the second plurality of camera pixels including single color information for one of a plurality of color channels;

detecting, by the processor, second spatial correlation of intensity information between a pair of the plurality of color channels in the second pixel data of a second array of the second plurality of camera pixels; and variably demosaicing, by the processor in response to the second spatial correlation, each camera pixel in the second array of the second plurality of camera pixels by scaling single color information of a camera pixel in the second array based on the second spatial correlation to generate second full color pixel data for the camera pixel in the second array of the second plurality of camera pixels.

21. The method of claim 20, wherein the first image is a left image of a stereo image and the first pixel data is left pixel data captured by left camera pixels, and wherein the second image is a right image of the stereo image and the second pixel data is right pixel data captured by right camera pixels.

22. The method of claim 21, further comprising:

outputting first full color pixel data for display on a left display of a stereo display device, and outputting second full color pixel data for display on a right display of the stereo display device.

* * * * *